US012761219B2

(12) United States Patent
Kloppstech et al.

(10) Patent No.: US 12,761,219 B2
(45) Date of Patent: Oct. 13, 2026

(54) DIGITAL SENSOR DEVICE FOR DETECTING ANALYTES IN A SAMPLE

(71) Applicant: digid GmbH, Mainz (DE)

(72) Inventors: Konstantin Kloppstech, Mainz (DE); Constantin Von Gersdorff, Mainz (DE); Nils Könne, Mainz (DE); Malte Köhler, Mainz (DE)

(73) Assignee: digid GmbH, Mainz (DE)

( * ) Notice: Subject to any disclaimer, the term of this patent is extended or adjusted under 35 U.S.C. 154(b) by 19 days.

(21) Appl. No.: 18/236,684

(22) Filed: Aug. 22, 2023

(65) Prior Publication Data

US 2024/0060972 A1 Feb. 22, 2024

(30) Foreign Application Priority Data

Aug. 22, 2022 (DE) ........................ 102022121187.8

(51) Int. Cl.
*G01N 33/543* (2006.01)
*G01N 33/569* (2006.01)

(52) U.S. Cl.
CPC ... *G01N 33/5438* (2013.01); *G01N 33/54346* (2013.01); *G01N 33/56983* (2013.01)

(58) Field of Classification Search
CPC .... G01N 33/00; G01N 33/48; G01N 33/5438; G01N 33/56983; G01N 2291/0255;
(Continued)

(56) References Cited

U.S. PATENT DOCUMENTS 6,575,020 B1 6/2003 de Charmoy Grey et al.
7,560,070 B1 * 7/2009 Baller .............. G01N 33/54373 73/1.01

(Continued)

FOREIGN PATENT DOCUMENTS

CN 1360521 A 7/2002
CN 1685233 A 10/2005

(Continued)

OTHER PUBLICATIONS

Rasmussen et al. "Cantilever surface stress sensors with single-crystalline silicon piezoresistors". Applied Physics etters, Research Article May 12, 2005.

(Continued)

*Primary Examiner* — C. Sun
(74) *Attorney, Agent, or Firm* — ArentFox Schiff LLP

(57) ABSTRACT

A sensor device is provided for the detection of an occurrence and/or a concentration and/or an amount of an analyte in a sample. The device includes a sensor, connection electronics and a housing. The sensor is configured to convert chemical and/or biochemical information from an analyte, preferably a virus, in a sample to an electrical signal. The sensor includes a test cantilever having a base and a deformable part, where a receptor layer for selective uptake of the analyte has been applied at least atop the deformable part. The sensor further includes a reference cantilever having a base and a deformable part, where a reference layer for selective non-uptake of the analyte has been applied atop the deformable part.

19 Claims, 15 Drawing Sheets

(58) Field of Classification Search
CPC ... G01N 2291/0256; G01N 2291/0427; G01N 29/022
See application file for complete search history.

(56) References Cited

U.S. PATENT DOCUMENTS

| | | | | |
|---|---|---|---|---|
| 2004/0152211 | A1 | 8/2004 | Majumdar et al. | |
| 2005/0276726 | A1 | 12/2005 | McGill et al. | |
| 2018/0074024 | A1 * | 3/2018 | Schlereth | H10N 30/302 |
| 2020/0033329 | A1 * | 1/2020 | Ndieyira | C23C 14/16 |
| 2020/0215537 | A1 * | 7/2020 | Ndieyira | B01L 3/5055 |

FOREIGN PATENT DOCUMENTS

| | | | | |
|---|---|---|---|---|
| DE | 10202010791 | U1 | 11/2000 | |
| DE | 60012962 | T2 | 8/2005 | |
| DE | 60215962 | T2 | 9/2007 | |
| WO | WO-9850773 | A2 * | 11/1998 | G01G 3/13 |
| WO | 2007088018 | A1 | 8/2007 | |

OTHER PUBLICATIONS

Office Action received for Chinese Patent Application No. 202311060048.7, mailed on Feb. 7, 2026, 21 pages of Original Document.

* cited by examiner

DIGITAL SENSOR DEVICE FOR DETECTING ANALYTES IN A SAMPLE

CROSS-REFERENCE TO RELATED APPLICATION

This application claims priority to and benefit of German Patent Application No. 10 2022 121 187.8 filed Aug. 22, 2022, the contents of which are incorporated by reference in their entirety.

TECHNICAL FIELD

The present invention relates to a sensor device for detecting one or more analytes in a sample in order to derive a qualitative and/or quantitative conclusion as to the occurrence and/or a concentration of the analyte(s) in the sample.

BACKGROUND

A highly sensitive method of detecting and analysing analytes in a sample involves using a microscopic deformation of a miniaturized spring element, called a cantilever, which is induced by an analyte in order to measure the presence of an analyte in a sample. A deformation caused specifically by an analyte is achieved in that the cantilever is provided on one side with a receptor layer that has binding molecules that bind specifically to a particular analyte to be examined and hence causes a unilaterally altered surface tension of the cantilever. The deformation of the cantilever is transformed, in particular by an electrical converter or transducer applied atop the cantilever, to an electrically detected parameter in order to quantitatively measure the presence of the analyte. Such a spring element is described, for example, in DE 10 2020 107 918 A1.

WO 2007/088018 A1 proposes spring elements for use in biosensors, for example for DNA analysis.

The deformation of cantilevers by different surface tensions is described, for example, in Rasmussen, P. A., Hansen, O., & Boisen, A. (2005) “Cantilever surface stress sensors with single-crystalline silicon piezoresistors” Applied Physics Letters, 86(20), 203502. https://doi.org/10.1063/1.1900299.

SUMMARY

In view of the foregoing, it is an object of the present invention to provide an improved sensor device for the detection of an analyte in a sample.

The object is achieved by a sensor device for detecting an analyte in a sample having the features of claim 1. Advantageous embodiments will become apparent from the dependent claims, the description and the figures.

Accordingly, a sensor for conversion of chemical and/or biochemical information from an analyte to an electrical signal in a sample is proposed. The sensor comprises a test cantilever having a base and a deformable part, with a receptor layer for selective uptake of the analyte applied at least atop the deformable part, wherein the test cantilever has a test converter layer comprising a passive test transducer on the base and an active test transducer on the deformable part, and wherein a test function layer is arranged between the test converter layer and the receptor layer. In addition, the sensor comprises a reference cantilever having a base and a deformable part, with a reference layer for selective non-uptake of the analyte applied atop the deformable part, wherein the reference cantilever has a reference converter layer comprising a passive reference transducer on the base and an active reference transducer on the deformable part, and wherein a reference function layer is arranged between the reference converter layer and the reference layer. The active and passive reference transducers and the active and passive test transducers are formed and configured to output an electrical signal corresponding to the occurrence and/or the concentration and/or the amount of the analyte(s) in the sample.

The base of the test cantilever and/or the base of the reference cantilever may be formed as a rigid base. A rigid base is understood to mean that a deformation of the respective cantilever, that is to say of the test cantilever and/or of the reference cantilever, does not occur to a substantial degree, if at all, in relation to the deformable part of the respective cantilever. The rigid base is, for example, connected to a substrate, supported by a substrate or machined from the substrate. The deformable part of the test cantilever and/or of the reference cantilever, by contrast, is not supported by the substrate, but rather formed so as to protrude beyond an edge of the substrate and in correspondingly free form.

The deformable part of the test cantilever and/or of the reference cantilever may be formed, for example, so as to be deflectable. The respective cantilever may, for example, be deflected about a bending edge formed in a transition region between base and deflectable region. The bending edge here is, for example, the edge of the substrate along which the cantilever is divided into the base and the deformable part.

However, the deformation of the respective cantilever in its deformable part is not limited to a lifting or lowering deformation, and the cantilever may also be deformed in and of itself, for example by bulging or crimping or contorting.

A sample here refers to a limited amount of a substance that has been taken from a greater amount of the substance, for instance from a reservoir, where the composition of the sample is representative of the composition of the substance in the reservoir and the corresponding occurrence in the reservoir can accordingly be inferred from the occurrence of the substance in and the substance compositions of the sample.

For example, a sample may be a saliva sample, or a blood sample, or lymph, or urine, or perspiration, or interstitial fluid, or a swab, in particular a throat swab or a nasal swab or a sinus swab, or removed tissue. A sample in particular comprises any kind of biological sample, i.e. in particular samples from animals as well.

A sample may also be a non-biological sample, for example a sample of a chemical substance.

An analyte here is the substance to be detected qualitatively and/or quantitatively in the sample or to be detected with the sensor. The analyte may in particular be present directly in the sample, or be dissolved in the sample, or adhere to the sample or to part of the sample, in particular to a sample particle. The analyte may also enter into a chemical, biological and/or physical interaction with the sample, such that the analyte is detectable only indirectly via a corresponding interaction.

One form of sample may in particular be converted to another form of sample, such that the analyte, or its presence, can be detected in a simple and reliable manner. For example, a swab may be dissolved in a liquid, such that the swab dissolved in the liquid is then the actual sample that is analysed for the analyte.

The analyte in the sample may also be chemically pretreated, for example—if the analyte is a virus—by opening the viral shell so as to gain access to nucleocapsid antigens.

The analyte may additionally be labelled by such pretreatment in order to amplify the measured signal. For this purpose, for example, conjugated antibodies may bind to antigens of the analyte in order to create maximum deformation in the cantilever system.

The sample then contains the chemical information and/or the biochemical information about the analyte. The chemical information may include, for example, the type of the analyte, the concentration of the analyte, the occurrence of the analyte, the weight of the analyte, the reactivity of the analyte, the density of the analyte, etc. The biochemical information comprises the same properties as the chemical information, except that these substances may arise, for example, from biological processes. In particular, reference is made to biochemical information when the analyte has a particular effect on the biological cycle, for example metabolism or the immune system.

The test cantilever and the reference cantilever each comprise a test converter layer and a reference converter layer into which the passive and active test transducer and reference transducer are embedded. The test converter layer and reference converter layer are configured primarily to electrically contact the passive and/or active test transducer and the passive and/or active reference transducer. The converter layers may also consist of two or more different layers and materials. In addition, the test converter layer and the reference converter layer may comprise further functions that will be discussed in detail later.

Preferably, a passive test transducer is arranged within the test converter layer on the base of the test cantilever and an active test transducer is arranged on the deformable part of the test cantilever, while a passive reference transducer is arranged within the reference converter layer on the base of the reference cantilever and an active reference transducer is arranged on the deformable part of the reference cantilever, where the active and passive reference transducers and the active and passive test transducers are formed and configured to output an electrical signal corresponding to the occurrence and/or concentration and/or the amount of the analyte in the sample.

The chemical and/or biological information is converted into an electrical signal. This may mean that an electrical signal may be changed by or constructed from the chemical composition of the analyte. This may relate, for example, to the conductivity of a circuit. For example, first biochemical information may be present when the circuit is conductive, and second biochemical information may be present when the circuit is not conductive or has reduced conductivity.

In addition to direct accessibility of the information, for example via conductivity, it is also possible to infer the biochemical information via a physical and/or chemical process and/or an interaction.

For this purpose, the proposed sensor comprises a reference cantilever and a test cantilever. A cantilever here is a spring element that has a base and a deformable part. The base is accordingly any mobile part of the cantilever, which is arranged on a substrate, in particular in a fixed manner. The deformable part of the cantilever is arranged on the base and projects beyond the base.

In particular, the base and the cantilever may be formed together in a one-piece design. In other words, the deformable part of the cantilever is suspended on the base at one end. Since the deformable part projects beyond the substrate, the deformable part of the cantilever can be bent, deflected and extended. The spatial limit from which the cantilever is bendable or the cantilever transitions from the base to the deformable part is called the bending edge. The bending edge is typically an edge of the substrate when the cantilever projects beyond the base.

If the cantilever is bent, this results in material stresses and forces in or on the cantilever material that can be measured. If such a material stress and/or force can be measured, it is possible to infer a deflection of the cantilever therefrom.

The transducers have the purpose of determining or of measuring the deformation of the cantilevers. The active transducers are arranged on the deformable parts of the cantilevers, whereas the passive transducers are arranged on the bases, for example the bases of the cantilevers. The transducers may in particular be used to influence electrical properties of a circuit.

For example, a deformation of the cantilever may have the effect of increasing the resistance of a transducer, for example the active transducer, while no deformation of the cantilever causes no change in the resistance of the transducer either. This may be achieved, for example, by building the transducers in accordance with the principle of a strain gauge, as a result of which a deformation of the respective cantilever is manifested in a change in length of the transducer strain gauge applied thereto, and hence it is possible to detect a deformation of the cantilever directly by a change in the resistance of the strain gauge.

The chemical and/or biochemical information from the analyte is thus detectable via a deformation of the cantilever, subsequent registration via a transducer, and finally via a change in an electrical property of a circuit.

The deformation of the cantilevers can be brought about in a substance-specific manner by means of a suitable coating. For that reason, the reference cantilever has a reference layer for selective non-uptake of the analyte, whereas the test cantilever has a receptor layer for uptake of the analyte.

A receptor layer here is a substance that can interact with the analyte. This in turn means that the receptor layer is chosen specifically for each analyte. Analogously, a reference layer is a substance that cannot interact with the analyte. The reference layer too is therefore chosen specifically for the analyte.

Interaction means that the analyte is in chemical and/or biochemical and/or physical interaction with the receptor layer. In particular, the interaction may consist in binding of the analyte to the receptor layer. An interaction may also consist in the absorption or adsorption or non-specific adhesion of the analyte to the receptor layer.

The receptor and reference layers are preferably chemically identical with regard to possible disruptive influences, and preferably differ solely by the interaction with the analyte. A substance that is not the analyte accordingly interacts just as strongly or just as weakly with the receptor layer as with the reference layer.

The effect of the selective uptake of the analyte on the test cantilever is that a force acts on the test cantilever as a result of the analyte, such that the test cantilever is sensitive to the analyte. Accordingly, the other substances in the sample that are not the analyte contribute merely to background noise in the form of background deflection of the test cantilever. The greater the concentration of the analyte in the sample or the faster the coverage of the cantilever surface with the analyte, for example, the faster and greater the increase in force on the test cantilever. A maximum force possible for the respective design is achieved when the cantilever is fully covered.

By contrast, the effect of the selective non-uptake of the analyte on the reference cantilever is that no force acts on the reference cantilever as a result of the analyte, such that only the substances that are not the analyte contribute to background noise in the form of background deflection of the reference cantilever.

This active force can bring about deformation in the deformable part of the test cantilever, while the deformable part of the reference cantilever is not deflected. The reason for the deflection of the cantilever is the change in surface tension caused by the interaction with the analyte. The change in surface tension leads to extension or contraction of the upper (or lower) surface of the cantilever. The different extension or contraction on the top and bottom sides results in an internal force or material stress in the material that leads to deformation.

Reference cantilevers according to the prior art merely have no receptor layer which is sensitive to the analyte. It is possible in this way to determine effects such as turbulence in the sample and thermal drift of the sensor system. However, in such a reference cantilever, the analyte can, for example, bind to the reference layer of the reference cantilever through non-specific binding. However, the analyte itself thereby contributes to the background noise. Therefore, in the case of a prior art sensor, there is a need for reference measurements in a reference sample, i.e. a sample without analytes. Only in this way can the effect of the non-specific binding of the substances that are not the analyte be established.

In the sensor according to the invention, the selective non-uptake of the analyte by the reference cantilever significantly simplifies the test method, since the reference cantilever is not sensitive to the analyte, and therefore the analyte does not contribute to the background noise either. Only the substances that are not the analyte contribute here to the background noise of the reference cantilever. The selective non-uptake of the analyte on the reference cantilever may be brought about to some degree in that the reference cantilever is exposed to the same turbulences, the same thermal drift and the same influence of all substances that are not the analyte as in a reference sample. The difference is, however, that the reference signal is determined directly in the sample liquid.

In particular, a reference cantilever with reference layer and a test cantilever with receptor layer results in distinctly more specific analysis of the analyte than just a reference cantilever without receptor layer, since both the reference layer and the receptor layer have a specific interaction or non-interaction with the analyte.

The structure of the sensor with reference cantilever and test cantilever has the advantage that two measurements can be undertaken simultaneously in the sample, and the measurement by the reference cantilever can calibrate the measurement by the test cantilever. This makes it possible to reduce environmental influences, for instance chemical, thermal, mechanical, electrical and fluidic disruptive influences, on the respective measurement, such that occurrence of the analyte can be inferred from the comparison of the measurement on the test cantilever and on the reference cantilever.

These forces or material stresses, for example extensions or contractions, that act on the cantilevers can ultimately be detected by the transducers, and stresses of different magnitudes are detected by the transducers through extensions or contractions of different magnitude.

In the sensor proposed here, the selective non-uptake of the analyte by the reference cantilever significantly simplifies the test method, since the reference cantilever is not sensitive to the analyte, and therefore the analyte does not contribute to the background noise either. Only the substances that are not the analyte contribute here to the background noise of the reference cantilever. The selective non-uptake of the analyte on the reference cantilever may be brought about to some degree in that the reference cantilever is exposed to the same turbulences, the same thermal drift and the same influence of all substances that are not the analyte as the test cantilever and also as in a reference sample. The difference is, however, that the reference signal is determined directly in the sample liquid.

In other words, rather than needing to calibrate the reference cantilever in a defined reference sample, the measurement with test cantilever and reference cantilever can be performed directly in the sample to be analysed.

In particular, a reference cantilever with reference layer and a test cantilever with receptor layer results in distinctly more specific analysis of the analyte than just a reference cantilever without reference layer, since both the reference layer and the receptor layer have a specific interaction or non-interaction with the analyte.

Since the active transducers are arranged on the deformable parts of the cantilevers, it is possible by means of the active transducers to find a measure that corresponds to the strength of the interaction of the analyte with the deformable part. The passive transducers on the other hand are arranged on the bases of the cantilevers, such that the interaction is reduced to those interactions that do not primarily cause deformation of the deformable part.

The structure of the sensor with reference cantilever and test cantilever has the advantage that two measurements can be undertaken simultaneously in the sample, and the measurement by the reference cantilever can calibrate the measurement by the test cantilever. This makes it possible to reduce environmental influences, for instance chemical, thermal, mechanical, electrical and fluidic disruptive influences, on the respective measurement, such that occurrence of the analyte can be inferred from the comparison of the measurement on the test cantilever and on the reference cantilever.

In particular, it is also possible to optimize the geometry of the reference cantilever for a specific interfering influence in order then to consider this interfering influence specifically in the evaluation. It is additionally also possible to determine different interfering influences with different reference cantilevers.

In other words, what is also proposed is a structure of the sensor with a test cantilever and at least two reference cantilevers, wherein the different reference cantilevers are then preferably optimized for different interfering influences.

The selective uptake of the analyte by the receptor layer and the selective non-uptake of the analyte, preferably of the virus, by the reference layer may cause a relative deflection of the test cantilever with respect to the reference cantilever, with inference of the occurrence of the analyte, preferably of the virus, preferably of the size of the occurrence, by comparison of the forces detected by the transducers.

In the proposed sensor, the sensor comprises a test function layer and/or a reference function layer arranged between the test convertible and the receptor layer and/or between the reference converter layer and the reference layer.

The function layer may fulfil a multitude of different functions, for example an improvement in the sensitivity of the sensor by shifting of the neutral axis and hence improvement of the extension at the site of the respective transducer or improvement in the surface quality for application of the receptor layer or of the reference layer or for adjustment of the surface energy, such that different receptor and reference layers can be applied in order to detect correspondingly different analytes. These functions mentioned by way of example are described in detail hereinafter.

The function layer may also be deposited onto the test converter layer and/or the reference converter layer for coverage such that this lies between the test converter layer or reference converter layer and a receptor layer or reference layer.

The deposition and structuring of the function layers can be conducted by a wide variety of different methods, for example by electron beam evaporation, sputtering deposition, electron beam lithography, plasma-enhanced chemical gas phase deposition (PECVD), chemical gas phase deposition (CVD), atomic layer deposition (ALD), by spin-coating by means of a spin-coating, inkjet printing, galvanic methods and/or other methods.

Typical materials for function layers may include binary silicon compounds (SiOx, SiN) and/or metal oxides (AlOx).

In particular, materials used for the function layers may be inorganic materials, for example at least one of the following materials: diamond, 3C-SiC, 6H-SiC, Si3N4, SiO2, SCSi (100), SCSi (110), poly-Si, tungsten, aluminium, nickel, copper, titanium, gold and/or Ni—Fe.

In particular, materials used for the function layers may also be organic materials such as SU8, polyimides, polyamides, PVDF, PMMA and/or SAMs (self-assembled monolayers).

The function layers may also be produced by electron beam evaporation with the following materials: Al, AlSiCu, Au, Cr, Ge, In, Mg, Mo, Ni, Pd, Pt, Ti, W, Si, SiO.

The function layers may also be produced by DC sputtering with the following materials: Al, AlCu(96/4), Co, Cr, CrNi(50/50), Cu, Mo, Ni, NiV7, Si, Sn, Ti, W, WTi(90/10), MoSi/SiC.

Function layers applied may also be dielectric layers comprising the following materials: Si3N4, SiO2, DLC, AN, a-Si.

The complete test converter layer and/or reference converter layer is preferably covered completely by the test function layer and/or the reference function layer, and hence covers all transducers. Alternatively, the cover, by virtue of the function layers, may also encompass only a portion of the converter layers, in which case at least one of the respective transducers of the respective cantilever is preferably covered.

If the test converter layer and/or the reference converter layer is covered by a respective function layer, a receptor layer or reference layer formed for uptake of an analyte cannot be applied directly to the test converter layer or reference converter layer since there would otherwise be no contact of the receptor layer or reference layer with the sample and hence with the analyte. Accordingly, for the detectability of an analyte by the sensor comprising function layers according to the present disclosure, a corresponding receptor layer or reference layer is applied to the outer surface of the test function layer or reference function layer. This has the particular advantage that the function layers can be optimized with regard to their surface for the receptor or reference layers deposited thereon. Details of this will be discussed later.

The coverage of the converter layers by means of the function layers prevent direct contact with any surrounding substances, liquids or gases that would have had direct contact with the converter layers in the case without covering function layers.

The outside influences include, for example, the (air) humidity surrounding the converter layers, changes in temperature of the environment of the converter layers or pH or the salt/ion concentration of media surrounding the converter layers. In general, any polar substance in a solution affects the dielectric properties of the solution, and is therefore counted as an outside influence. In addition, mention should also be made of the influence of air gases in the air surrounding the converter layers or of the analytes dissolved in the sample. Particular mention should be made here of the finite conductivity of solutions that surround the converter layers and in which the analytes are dissolved. In general, the contact of the converter layers, especially of the transducers embedded therein, with conductive media leads to greater sensor noise and should therefore preferably be avoided.

The aforementioned influences especially result in increased drift of the sensor signal in the absence of function layers. Drift of the sensor signal here means that the electrical parameter of the transducers which is to be detected varies over time because of variation in the outside influences on the transducers, even though the presence or concentration of the analyte has not changed. In other words, variation in the outside influences that are not the analyte may be associated with variation in the sensor signal. This can have the effect of an incorrect conclusion of a change in the presence or concentration of the analyte or of absence of the analyte. The provision of the function layer(s) proposed here can reduce or prevent such drift of the sensor signal because of outside influences, so as to improve accuracy and reliability of detection of the analyte.

The external influences can also lead to greater sensor noise, which worsens the signal-to-noise ratio or even results in loss of sensitivity in the sensor. The proposed function layer(s) can make the signal-to-noise ratio more constant or keep it constant.

Moreover, the outside influences mentioned can result in ageing effects of the transducers, which alters the corresponding electrical measurement parameter which is utilized as a parameter for detection of the analyte in the sample in a sustained manner such that risk-free or reliable operation of the sensor is no longer possible. The proposed function layer(s) can also reduce or prevent ageing effects of the transducers, such that the sensor enables more reliable detection of the analyte.

Accordingly, the covered transducers, by virtue of the protective function layers, especially by virtue of suppressed oxygen content, air humidity, etc., do not have any significant ageing effects, if any at all, for example drift of the sensor signal and/or deterioration in the signal-to-noise ratio.

In addition, the function layers can protect the converter layers from outside influences that are induced, for example, by reactive media surrounding the converter layers, especially by acids or reactive gases. This especially prevents what is called chemoristic behaviour of the transducers. What is meant by chemoristic behaviour is that a material changes its electrical resistance in response to a chemical environment close to or in contact with the material.

What is not ruled out, however, is the use of porous function layers that are characterized in that the function layers are partly permeable to particular substances. Accordingly, chemoristic behaviour can be exploited specifically in that transducers covered by a porous function layer gain specific selectivity with respect to one or more analytes that can pass through the porous function layer to the transducer.

It is also possible here, for example, to use different functions layers with different properties with regard to their partial permeability.

The function layers have preferably been produced from an electrically insulating material having high insulation resistance. This is more preferably the case for the function layer(s) that are in direct contact with the transducers and/or the electrodes. In addition, the test function layer and the reference function layer may have been produced from the same material.

Operation of the transducers, in particular for readout of the electrical measurement parameters to be detected, typically requires electrical voltages that drop across the electrodes of the transducers. In the absence of an insulating test function layer or reference function layer that covers the test converter layer or reference converter layer, the electrical potentials associated with the voltages have a direct effect on the test converter layer or reference converter layer, especially at the electrodes of the transducers.

Since the converter layers without insulating function layers, for detectability of an analyte by the sensor, would also have to comprise a receptor layer or reference layer for selective uptake or non-uptake of an analyte to be detected, the binder molecules of the receptor layer (for example antibodies) or reference layer and the analytes bound to the converter layers would likewise be affected by the electrical potentials that exist in the converter layers, for example in their binding properties (specificity, binding rates, binding capacity etc.).

If, for example, a test cantilever and/or reference cantilever with test converter layer and/or reference converter layer and a receptor layer and/or reference layer, but without protective test function layer and/or reference function layer, were to be brought into contact with a sample, the voltage drop across the electrodes of the active and/or passive transducers, as well the electrical current that flows through the transducers, may result in a low but finite leakage current that flows, for example, through the high but finite resistance of the sample material, or example a liquid solution. The chemicals present in the sample, and the binding molecules of the receptor layer and/or reference layer (that are themselves chemicals), are then exposed to an electrical voltage or electrical leakage current that can lead to electrochemical reactions of the chemicals involved. Correspondingly, electrochemically induced changes in said chemicals can have an influence on the electrical signals of the transducers.

Insulating function layers that cover the converter layers have the crucial benefit that electrochemical reactions that would arise in the case without an insulating function layer, especially at the electrodes of the transducers, through direct contact of the transducers with the sample are suppressed. In other words, by virtue of the function layers, the surface of the function layers which is configured by correspondingly formed subsequent layers (for example a receptor layer or reference layer) for uptake or non-uptake of a specific analyte is essentially free of electrical potentials and hence of the electrochemical reactions.

The absence of electrochemical reactions in the converter layers has the consequence that electrical signals from the transducers cannot be affected by such reactions, and those changes in the electrical signals that are induced by the analyte to be examined are not masked by electrochemically induced signals. This improves the sensitivity of the transducers and hence of the sensor. In particular, the noise characteristics of the transducers are improved, which improves the signal-to-noise ratio of the sensor.

The test function layer and/or reference function layer arranged between the test converter layer and/or the reference converter layer and the receptor layer and/or the reference layer insulates the receptor layer and/or the reference layer and its binding molecules, especially proteins, for example antibodies, from the electrical voltages that drop across the transducers or along the converter layers. Accordingly, any influence induced by electrical voltages on the receptor layer and/or reference layer and its binding molecules owing to electrochemical reactions is suppressed.

The coating of a cantilever with a receptor layer or reference layer, where the receptor layer or reference layer is in direct contact with the respective converter layer and hence with the active and/or passive transducer, can result in disruptive influences by the transducers. Using the function layer arranged between the converter layers and the receptor layer or reference layer, such disruptive influences by the coating are suppressed.

The region of the converter layer covered by the function layers can additionally serve as protection from electrostatic discharge effects in the converter layers. A converter layer exposed to the environment that does not have any protective function layers, especially in the case of an electrically conductive layer for electrical contact connection of the transducers, may be susceptible to electrical discharges that can arise as a result of any electrical potentials in the immediate environment of the converter layers. The insulating function layers that cover the converter layer can prevent said discharges across the conductive layer of the converter layers or across the electrodes of the transducers. Such protection is strong particularly in embodiments with high insulation resistances of the function layers, and can prevent discharges even at high potentials.

In a particularly preferred embodiment, the converter layers are formed as electrically conductive layers that are structured to form electrodes, such that the active and passive transducers can be electrically connected externally. A particular benefit of function layers covering the transducer layers is that non-inert materials are also suitable as conductive layers since there is no exposure to the environment by virtue of the function layers and, in particular, the oxidation of reactive materials is suppressed.

In addition, the converter layers, as well as conductive layers as described above, also include activation layers that are configured to bring about an increase in surface voltage along the converter layers. The covering function layers enable the utilization of non-inert materials too as activation layer.

In a particularly preferred embodiment, the converter layers formed as activation layers can simultaneously function as electrically conductive layers for the electrical connection of the transducers. Accordingly, the activation layer may also have been produced from an electrically conductive material, in particular from gold, in which case an adhesion promoter, for example titanium, is used between the gold layer and the cantilever material because gold only has poor wetting capacity on the surface of the cantilever. As described above, however, non-inert materials are also suitable by virtue of the protective function layers. Accordingly, the selection of material for activation layers is significantly increased and, given a suitable choice of material, it is also possible to dispense with an adhesion promoter.

A further function of the function layers is to increase the variability of the sensor with regard to suitable receptor layers or reference layers for specific detection or non-detection of an analyte in a sample, and to increase the sensitivity of the sensor.

The object is likewise achieved by function layers arranged between the converter layers and the receptor layer or reference layer.

In the absence of function layers, the converter layers of the cantilevers must have particular properties in order that a subsequent receptor layer or reference layer wets the underlying converter layers in such a way as to ensure suitable adhesion between the layers.

Adhesion/wetting of a layer requires the surface energy of the layer to be wetted to be much greater than the surface energy of the wetted layer. Accordingly, in the case without function layers, the converter layers, as well as the activation property and/or the electrically conductive property and/or the inert property, must also have such a surface energy that a subsequent receptor layer or reference layer adheres to the respective converter layer. This significantly limits the choice of suitable materials for the converter layers and the receptor layer or reference layer.

Accordingly, if function layers are arranged between the converter layers and the receptor layer or reference layer, it is merely necessary to adjust the surface energy of the function layers to the surface energy of the receptor layer or reference layer in order to assure suitable wetting/adhesion between the layers. This significantly increases the possible selection of converter layers, as already set out above, but also the selection options for the receptor layers or reference layers. In particular, the function layers may be matched to any desired receptor layers or reference layers.

In a typical embodiment, a passivation layer may be provided atop the lower surface of the cantilevers. The passivation layer is configured to minimize non-specific adhesion of an analyte on the underside of the cantilever.

However, it is also possible in a preferred embodiment that a receptor layer for selective uptake of an analyte is present on the function layers and also on the underside of the respective cantilevers, in which case the change in surface tension of the upper layer as a result of binding of an analyte to the receptor layers is the opposite of the change in surface tension of the lower layer.

In this embodiment, the deformation is increased as a result of the analytes of the upper and lower surfaces of the cantilever that bind to the binding molecules of the receptor layers, such that the electrical signals generated by the active test transducer are likewise amplified, which increases the sensitivity of the sensor.

In addition, the mechanical stress state of the cantilever can be controlled by means of the construction proposed.

In a particularly preferred case, the stress field of a cantilever in the case of deformation thereof is configured such that extension/contraction is at a maximum at the site of the active test transducer and/or of the active reference transducer, such that the electrical signals of the active test transducer and/or active reference transducer are also maximized.

This includes both longitudinal extension and transverse extension of the cantilevers, and any combinations of the two. Accordingly, the transducers are preferably configured to be sensitive to both directions of extension. The terms "extension" or "deformation" accordingly include longitudinal and transverse extensions and mixed extensions.

The neutral plane corresponds to that theoretical surface contour within a material, for example a cantilever, along which no elongation/contraction occurs because of a surface tension on the material. The neutral plane is formed by two mutually perpendicular neutral axes. The neutral axes correspond to both theoretical lines in longitudinal/transverse direction that do not undergo any extension/contraction as a result of longitudinal or transverse stress along the surface of the cantilever. Accordingly, sites at a position particularly far removed from the neutral plane or the axes are subject to particularly high extension/contraction.

With the aid of the function layers that are arranged atop the converter layers and therefore preferably cover the transducers or individual transducers, it is possible to additionally adjust the distribution of extension of the cantilevers.

For example, considering the extension in a selected direction, for example in the longitudinal direction of the cantilever, the position of the longitudinal neutral axis can be specified qualitatively in said direction. Accordingly, the geometric lengthy of the neutral axis, for a structure consisting of two layers having thicknesses h 1 and h 2, can be expressed as:

$$\bar{y} = \frac{h_1 + h_2}{2}\left(\frac{\lambda}{1+\lambda} + \frac{E_2}{E_2 + \lambda E_1}\right),$$

where $\lambda = h_1/h_2$ represents the thickness ratio of the layers and $E_1$ and $E_2$ represent the moduli of elasticity of the layers. For isotropic materials, the moduli of elasticity of which are likewise isotropic, the position of the transverse neutral axis is correspondingly equivalent, and the result is a flat contour of the plane (provided that the thicknesses of the layers are homogeneous). However, anisotropic materials having correspondingly anisotropic moduli of elasticity lead to a non-trivial contour of the neutral plane.

Accordingly, as per the above equation, for example, moduli of elasticity of the function layers may be chosen such that the neutral plane or the neutral axes of the cantilevers are shifted downward, i.e. in the direction away from the converter layers or the transducers, so as to maximize extension at the site of the transducers under deformation. For this embodiment, the modulus of elasticity of the function layers may thus be chosen to be sufficiently much smaller than the average modulus of elasticity of the layers beneath. A stress in the cantilevers which is induced by different moduli of elasticity of different layers is also referred to as intrinsic prestress or intrinsic stress.

It is preferably possible to choose the modulus of elasticity of the function layers to be particularly small, in particular smaller than the modulus of elasticity of the converter layers beneath and/or of the main body of the cantilevers. In general, the modulus of elasticity of the function layers, however, can be chosen as desired in order to cause or establish a particular stress distribution of the cantilever under deformation.

It is also possible according to the above equation to use the thickness of the function layers in order to affect the position of the neutral plane or axes of the cantilevers. The neutral plane, with ever greater thickness, moves in the direction of the function layers, i.e. toward the converter layers. Accordingly, smaller thicknesses should be chosen for the inverse effect.

Accordingly, in a further embodiment, suitable structuring of the function layers can maximize a distribution of stress in a cantilever which is induced by deformation of the deformable part of the cantilever along the converter layers, in particular at the site of the active transducers. Structuring of the function layers here means controlled variation of the height profile of the function layers.

For example, the function layers at the site of the transducers can be achieved by structuring, where the height profile of the function layers is altered such that the stress state at the site of the transducers is maximized. This can be effected, for example, in that the thickness of the function layers is reduced, for example by controlled local etching of the function layers at the site of the transducers, such that the neutral plane of the respective cantilever moves away from the transducer at said sites, which increases the extension at the site of the transducers under deformation.

By application of activation layers, the respective cantilevers may also have a stress state that leads to such high intrinsic prestress that the respective cantilever is significantly bent even in the equilibrium state, i.e. without analytes binding to the receptor layer or reference layer.

In this case, it is advantageous when the stress state can be converted to a neutral, preferably straight, equilibrium state of the cantilevers. The latter can be achieved via the additional function layers in that the material properties of the function layers, especially the thickness and/or modulus of elasticity thereof, are adjusted such that a bent state of the cantilevers is converted to a neutral, preferably straight, state.

In addition, it is also possible to use a suitable structuring of the function layers in order to achieve a stress-free state of the cantilevers at equilibrium, i.e. to counteract any intrinsic prestress in the cantilevers.

For further optimization, especially maximization of the tension or change in length of the cantilevers, especially at the position of the transducers, it is also possible in a further embodiment to influence the structure of the transducers themselves in order to adjust the stress state of the transducers in the event of bending of the cantilevers.

For this purpose, it is sensible to quantify the structural change in resistance of the transducers. The k-value, also called gauge factor, is the proportionality constant between the extension of the transducer and its change in resistance:

$$\frac{\Delta R}{R} = k\left(G_L\frac{\Delta L_l}{L_l} + G_T\frac{\Delta L_t}{L_t}\right),$$

where ΔR is the change in resistance of the transducer, R is the resistance of the transducer when the cantilever is not bent, $\Delta L_l$ and $\Delta L_t$ are the longitudinal and transverse changes in transducer length, while $L_l$ and $L_t$ are the longitudinal and transverse lengths of the transducer when the cantilever is not bent. The mutually orthogonal changes in length are weighted by the weighting factors $G_L$ and $G_R$, where these are determined in turn by the geometric configuration of the transducers. In particular, it is also possible to measure any other measured variables proportional to the k value or to resistance, for example conductivity.

The k value may also be directional in the case of an anisotropic material.

Firstly, the transducers may be structured in terms of their shape in the plane of the converter layers. A change in shape of the transducers in the plane can create a stress distribution that generates a greater electrical signal in the case of deformation of the cantilevers. Accordingly, the structuring may be chosen so as to maximize the change in length at the positions of the transducers on deformation of the cantilevers.

Specifically, according to the above equation, the geometric weighting factors $G_L$ and $G_T$ may be influenced directly by structuring of the transducers as described above. According to the desired sensitivity in longitudinal and/or transverse direction, suitable structuring of the transducers may be undertaken in order to increase or lower the weighting factors.

Secondly, the transducers may also be structured in terms of their height profile. In this case, in particular, the height profile of a transducer is configured such that it differs from a flat profile. Structuring of the height profile of the sensor can achieve very specific influencing of the stress state of the transducer. As described above, a variation in thickness of the transducers caused by the structuring induces a shift in the neutral plane or axes, and hence a change in the stress state or in the change in length at the site of the transducers when externally induced bending of the cantilevers occurs. The height profile is preferably configured such that the change in length is maximized in the case of bending of the cantilevers.

It is likewise possible to simultaneously structure the transducers in terms of their structure in the plane of the converter layers and also with regard to their height profile, in order to achieve a desired stress distribution in the transducers.

The reference and test cantilevers may have a further layer that comprises a self-assembly monolayer.

A self-assembly monolayer can in particular reduce unevenness on the underlying surface and compensate for chemical variations, such that uniform coating of the cantilevers with the receptor or reference layer is possible. The homogeneous surface properties of the cantilevers thus ultimately make it possible to improve the binding properties of the receptor layer and of the analytes.

Accordingly, the self-assembly monolayer may be arranged between the test function layer and/or the reference function layer and the receptor layer and/or the reference layer.

The transducers may be formed and configured to ascertain deformations of the deformable parts of the test cantilever and of the reference cantilever, preferably to detect the forces exerted in each case on the bases and the deformable parts of the test and reference cantilevers on deformation.

If a sensor, consisting of a reference cantilever and a test cantilever with the reference layer and the receptor layer respectively, is exposed to a sample that comprises an analyte, the interaction may involve binding of the analyte to the receptor layer.

The binding of the analyte to the receptor layer changes the surface tension of that side of the test cantilever covered by the receptor layer, which leads to a force on the test cantilever, whereas the analyte does not result in any force acting on the reference cantilever. The greater the concentration of the analyte in the sample or the faster the coverage of the cantilever surface with the analyte, for example, the faster the increase in force on the test cantilever. In order to measure the concentration of the analyte, it is thus possible, for example, to measure the slope of the continuous change in force over time on the test cantilever. A maximum force possible for the respective design is achieved when the cantilever is fully covered.

This interaction may bring about a deformation in the deformable part of the test cantilever, while the deformable part of the reference cantilever is not bent.

The reason for the deflection of the cantilever is the change in surface tension caused by the interaction with the analyte. The change in surface tension leads to extension or contraction of the upper (or lower) surface of the cantilever. The different extension or contraction on the top and bottom sides results in an internal force or material stress in the material that leads to deformation.

These forces or material stresses and in particular extensions or contractions may ultimately be detected by the transducers, wherein stresses of different magnitudes are detected by the transducers through extensions or contractions of different magnitude. The respective transducer changes its resistance in accordance with the extensions or contractions, such that the transducer serves in this way to detect the extensions or contractions.

The force to be detected may be a bending force and/or an extension force and/or a contraction force and/or a shear force and/or be based on the modulus of elasticity of the reference cantilevers and test cantilevers. In general, the force to be detected is not induced by a surface tension on the surface of the cantilevers.

A bending force may bring about a change in the geometry of the cantilever, in particular impose a curvature on the cantilever that differs from the unstressed cantilever. Such a curvature may lead to the occurrence of bending moments or extensions and thus to bending stresses that can be determined with an appropriate transducer.

The change in the surface tension and the resulting extension force may in particular cause a change in length of the cantilever in this region. The extension on the upper surface may in particular be different from the lower surface of the cantilever. The upper surface may in particular extend parallel to the base of the cantilever (called a transverse extension) or perpendicular to the base of the cantilever (called a longitudinal extension), or extend in a combination of the two directions. The magnitude of the extension here is strongly dependent on the geometry of the cantilevers and of the other layers provided on the surfaces, for example the electrodes, such that optimal detection of the analyte can be achieved by optimization of alignment and cantilever geometry. In particular, the length, width and thickness profile of all involved layers of the cantilever are significant here. The respective change in length may be different depending on the direction of the crystal lattice of the cantilever.

The relative deformation and/or the relative change in surface tension, in the case of unstructured transducers, runs in a longitudinal direction (i.e. in the direction of longitudinal extension) of the test cantilever and/or of the reference cantilever, where longitudinal direction runs perpendicular to the base of the test cantilever and/or of the reference cantilever, where the active and passive test transducers and/or the active and passive reference transducers are preferably aligned in longitudinal direction and hence are of maximum sensitivity in said direction.

Particular preference is given, however, to the case of structured transducers as described above, for which relative deformation and/or relative change in surface tension run in longitudinal and transverse direction of the test cantilever and/or reference cantilever, where the active and passive test transducers and/or the active and passive reference transducers are optimized with regard to sensitivity by suitable geometric structuring in both directions.

If the extension force is different on the upper surface and the lower surface, the acting force is also referred to as shear force.

A bending force is active in the case of a bent cantilever. This extends the upper surface of the cantilever, and this extension is in particular greater than on the lower surface of the cantilever (which is in particular contracted), such that a shear force acts overall on the cantilever. In the case of a (hypothetical) homogeneous cantilever, extension on the top side would be the same as contraction on the bottom side. In the case of an asymmetric construction of the cantilever by virtue of the layer system proposed, extension on the top side has a different value to contraction on the bottom side.

The abovementioned forces are all based on what is called the modulus of elasticity of the cantilever. The modulus of elasticity of the cantilever is a material constant that is specific to the material used for the cantilever. By choice of the material or material composition or by processing the material, it is possible to set the modulus of elasticity within a particular range, such that the effect to be measured can be optimized for the respective transducer setup. Conversely, it is of course also possible to adapt the transducers to the existing modulus of elasticity of the material and to optimize their sensitivity.

The cantilevers may preferably be multilayer cantilevers, for example cantilevers made of a gold layer and the silicon nitride layer, and a function layer atop the gold layer. A cantilever of this kind consists of material layers that together have a defined stress state. For example, the state may be stress-free, such that the intrinsic mechanical stresses are minimal. But it may also be the case that a multilayer cantilever is prestressed, such that the cantilever is particularly sensitive to a change in surface tension. It may additionally also be the case that a homogeneous cantilever is coated differently on the upper side and the lower side in order to obtained the desired effect resulting from multilayer cantilevers.

By comparing the deformations and/or forces detected by the transducers, it is possible to infer an effect, caused by the selective uptake of the analyte, on the test cantilever, and hence the occurrence thereof. It is preferably possible to infer the magnitude of the occurrence.

In particular, the passive transducers at the bases of the cantilever can only detect effects that are primarily not a deflection since the bases are coupled fixedly to the substrate. The measured signals from the passive transducers thus yield a basic signal that is specific to the respective cantilever.

For example, the base of the reference cantilever, influenced by the environmental conditions, may cause a first electrical state of the passive reference transducer, while the interaction of the test cantilever with the sample causes a second electrical state of the passive test transducer.

The active transducers on the deformable parts of the cantilevers by contrast indicate an extent of the deformation or acting force and thus also indirectly an extent of the interaction of the reference layer or receptor layer with the analyte and the other substances in the sample.

For example, the reference cantilever may be bent by a first amount as a result of interaction with the sample, such that the deflection causes a third electrical state in the active reference transducer, whereas the test cantilever is bent by a second amount as a result of interaction with the sample and is bent by the third amount as a result of additional interaction with the analyte in the sample, which causes a fourth electrical state in the active test transducer.

Comparison of the electrical states of the passive and active transducers indicates an extent of the deformation of the cantilevers, where the electrical signal from the active transducers is corrected to the base signal from the passive transducers on the base. At the same time, a comparison of the measured signals from the active transducers gives an extent of the difference between the deformation of the cantilevers. This makes it possible to infer a specific influence of an analyte on the test cantilever.

The structure with four transducers has the advantage that such local calibration of the sensor is possible at the location of the influence of the sample and of the analyte.

The deformable parts of the reference and test cantilevers may have identical geometric dimensions, where the width of the deformable part of the reference and test cantilevers corresponds to the length of the deformable part of the reference and test cantilevers.

This makes it possible to generate a particularly large force on the active transducers through the deformation of the cantilevers.

The bases of the reference and test cantilevers may be arranged on the same overall base. In particular, the test cantilever and the reference cantilever have a common base.

This makes it possible to achieve the effect that the passive transducers operate at a similar base level, in that influences that would be specific to the separate bases are reduced. This may lead to greater measurement accuracy.

In particular, the reference and test cantilevers may thus be arranged particularly close to one another, for example less than the width of one cantilever.

This can achieve the effect that identical interfering influences act on the cantilevers, these being caused for example by a temperature difference in the sample, in particular by convection or another fluid dynamic.

In addition, it is also possible to achieve the effect that multiple cantilevers can be produced from one (silicon) wafer.

In addition, the distance of the cantilevers from the production limit may be optimized. The production limit is typically defined by the spotting distance, where the spotting distance is a measure of relevance when producing the reference layer and receptor layer; see below.

The bases of the reference and test cantilever may have a one-piece design.

This makes it possible to achieve the effect that the base-specific influences are reduced further, such that greater measurement accuracy is achieved. In addition, this enables simpler production of the cantilever pair or of a multitude of cantilever pairs.

The deformable parts of the reference and test cantilevers may thus in particular have identical geometric dimensions, where the width of the deformable parts of the reference and test cantilevers corresponds to the length of the deformable parts of the reference and test cantilevers, the bases of the reference and test cantilevers are arranged on the same overall base, and the bases preferably have a one-piece design.

The reference and test cantilevers may comprise $Si_3N_4$, $SiO_2$, $Si_3N_4/SiO_2$, SiC, Si or consist of Si or comprise a polymer.

The silicon-based reference and test cantilevers make it possible to use production methods known from the semiconductor industry, thus enabling the production of sensors according to the invention on a large industrial scale. Polymers may likewise be produced on a large industrial scale and have the advantage that their material properties can be predetermined to a large degree.

The transducers may have identical intrinsic physical properties, where the transducers are configured to adjust their electrical properties, preferably the electrical resistance or another value proportional to the k value (see equation above), in accordance with the forces acting on the reference and test cantilevers.

Identical intrinsic physical properties here include those properties that are responsible for the measurement properties of the transducer on a cantilever. This especially relates to a voltage that can drop across the transducer, i.e. the resistance or the conductivity of the transducer. The resistance depends in particular on the geometry of the transducer, such that, in the case of uniform conductivity of the various transducers, the geometry of the transducers accordingly has to be identical. However, nonuniform conductivity of the various transducers may be caused by altered nanoscopic material properties of the transducer materials.

But the physical properties also relate to the way in which the measured signal changes in reaction to an acting force. Each transducer should in particular react identically to an identical exerted force or deformation of the cantilever, such that no non-linear deviations can occur between the various transducers.

The intrinsic physical properties are defined in particular by the nanostructure of the transducers. The nanostructures are preferably identical for all transducers, such that identical geometric configurations give identical physical properties.

Particularly high sensitivity can be achieved especially in that the metal particle size of the transducers is at a minimum.

A reliable production process for the transducers can thus ensure that all transducers react identically to a force or an external disruptive influence, such that variances in the different forces measured are based solely on the external action on the cantilevers and do not depend on the intrinsic physical properties.

In particular, the electrical properties of the transducers can ultimately be used to infer the bending states of the individual reference and test cantilevers, and it is possible in particular to infer the occurrence of the analyte taken up selectively by the receptor layer. The transducers, which perceive an interaction with the analyte indirectly via the cantilever, vary their measurement properties in accordance with the acting forces.

The distance between the active reference transducer or test transducer and the passive reference transducer or test transducer may be less than 100 μm, where the transducers may adjoin the bending edge.

Since the transducers are placed as close as possible to one another, spatial influences on the transducers that stem from the sample are reduced. If, for example, the occurrence of the analyte in the sample is subject to a particular concentration gradient, it is advantageous to perform the measurements at one point on the gradient as far as possible.

The smallest possible distance is achieved when the transducers adjoin the bending edge. The bending edge here is the edge of the substrate along which the cantilever is divided into the base and the deformable part. For example, the active transducers may adjoin the bending edge by their lower edge, while the passive transducers may adjoin the bending edge by their upper edge.

In particular, the optimal distance between the active transducers and the bending edge may depend on the exact geometric shape of the sensor. The distance to the bending edge may accordingly be chosen such that a surface extension creates a maximum change in the electronic state of the transducer.

In particular, the optimal distance between the passive transducers and the bending edge is achieved when the deflection of the test cantilever achieves the smallest possible change in the electronic state of the test transducer.

In particular, however, the active and passive transducers should be arranged sufficiently close to one another that they can be produced easily and quickly in one step in a production process, for example in a scanning electron microscope-based or electron lithography production process, without any need for mechanical movement of an XYZ stage device to move the wafer. This in particular enables distinctly faster and more accurate and also inexpensive production of the sensors.

In particular, the orientation and geometry of the transducers determines whether longitudinal extension, transverse extension or mixed extension of the cantilevers is measured. If a longitudinal axis of the transducer runs parallel to the base, preference is given to measuring a transverse extension of the cantilever. If a longitudinal axis of the transducer is oriented perpendicular to the base, preference is given to measuring the longitudinal extension of the cantilever. The longitudinal axis of a transducer may alternatively have any orientation with respect to the base and correspondingly measure mixed extension (a superposition of longitudinal and transverse extension). It is therefore in particular also possible to form rectangular, square, round, convex or concave transducers in order to adjust the sensitivity of the transducer to the cantilever geometry.

The reference and test cantilevers, and the active and passive reference and test transducers, may be in a mirror-symmetric arrangement relative to one another.

The mirror symmetry may relate in particular to a mirror axis arranged between the reference transducer and the test transducer.

A mirror-symmetric structure makes it possible to reduce influences, for example of electrical voltages, on the transducers, or at least to guide them symmetrically to one another. This can improve measurement accuracy and susceptibility to interfering influences.

The test converter layer and reference converter layer of the sensor may comprise electrodes, preferably four electrodes, that are configured to make electrical contact with the active and/or passive test transducers and the passive and/or active reference transducers.

An electrode here is a conductive layer, for example made of gold, or a wire or cable which, from a connection end of the transducer, can make an electrically conductive connection to an external device, for example a current or voltage source, or to a corresponding measurement device. In principle, any conductive connection between the transducer and the external device may be regarded as an electrode. However, an electrode is considered here in particular to be the part of the electrical connection that contacts the sensor.

An electrical connection is typically implemented from the sensor to an external source or a measurement device via an electrical terminal. In this case, an electrical terminal plug is contacted by a cable or a wire to what is called a bonding pad, for example in that the wire is fixedly ultrasonically welded thereto. An electrical connection then leads directly from the bonding pad to the transducer. The electrical isopotential surface between the transducer and the bonding pad is called electrode hereinafter.

The electrode serves to make electrical contact with the transducers and in particular to make it possible to route the electrical signals from the sensor to a measuring device.

The electrodes may in particular be at different electrical potentials and interact with one another thereby. In order to minimize this mutual influencing of the electric currents and voltages in the electrodes, it is therefore advantageous for the electrodes likewise to have a symmetrical form such that the respective interference is at least distributed uniformly throughout the system. This may in particular be achieved by using an even number of electrodes or using only four electrodes in the case of four transducers.

Due to the form of the electrode geometry, it is therefore possible for the basic signal level that arises at the electrodes due to any potential differences to be less than 1.1 V, such that it is not necessary to electrically encapsulate the electrodes. Electrical encapsulation may be understood here, for example, as electrical insulation or covering or shielding of the electrodes and of the bonding wires. This can simplify the production process and improve measurement accuracy.

The distance between the electrodes may be minimal.

The distance is minimal here when the electrodes are not in contact, i.e. are not conductively connected to one another. In other words, the conductance between the electrodes is significantly lower than the conductance of the transducers.

Since the distance between the electrodes is minimal, it is possible to place more electrodes on a wafer, thereby enabling a cost-effective production process. In particular, however, this can also reduce the size of the transducers, such that the influence of non-uniform environmental conditions on the transducers can be further reduced.

The transducers may be electrically interconnected in a full bridge, where the full bridge is configured to establish a cross-bridge voltage based on the electrical properties of the transducers, in particular in the event of an asymmetric change in the electrical properties of the transducers.

A full bridge here is a measuring apparatus for measuring electrical resistances or small changes in resistance. A full bridge is also known by the names Wheatstone bridge or H-bridge or symmetrical full bridge or thermo-symmetrical full bridge.

For example, the active and passive transducers of the reference and test cantilevers are interconnected to form a full bridge in that each terminal contact of the active transducers is set to a common potential via a first electrode. In addition, a respective terminal contact of the passive transducers is set to a common potential via a third electrode. A voltage (DC or AC voltage) may be applied via these first and third electrodes, and the combination of the active transducers or of the passive transducers in each case acts as a voltage divider in accordance with the resistances of the respective transducers.

In addition, on each cantilever, the further terminal contact of the active transducer is connected to the further terminal contact of the passive transducer via a second electrode in the case of the test cantilever or fourth electrode in the case of the reference cantilever. A cross-bridge voltage is accordingly established across the second and fourth electrodes if the ratio of the resistances of the active transducer to the passive transducer of the reference cantilever is not the same as the ratio of the resistances of the active transducer to the passive transducer of the test cantilever.

In the ground state of the full bridge of the sensor, the cross-bridge voltage is ideally equal to zero, since no force or an identical force acts on all the transducers involved. This ground state is preferably established at the early stage of the production process, such that only a small offset voltage that can be compensated for by means of a measurement setup is established between the electrodes.

Proceeding from this ground state of full bridge, asymmetric changes in force can then preferably be detected. If, for example, the active test transducer of the test cantilever reacts to an exerted force with a change in its electrical property, or with a change in its electrical resistance, the ratio of the resistances in the full bridge is no longer balanced, such that a cross-bridge voltage is established. The cross-bridge voltage established can ultimately be detected with a measurement device.

In particular, no cross-bridge voltage is established when the exerted force on the active transducers of the test cantilever and of the reference cantilever is the same.

However, this is then a non-specific exerted force that does not stem from a specific interaction with the test cantilever. In particular, no cross-bridge voltage is established when the exerted force on the passive transducers of the test cantilever and of the reference cantilever is the same.

By virtue of implementation as a full bridge, calibration of the active test transducer of the test cantilever is effectively brought about via the active reference transducer of the reference cantilever. The passive transducers firstly enable calibration to the ground state of the full bridge; secondly, deflection of the deformable parts of the cantilevers can be inferred by comparing the active and passive transducers.

The sensor may comprise a cross-bridge voltage detector configured to detect the cross-bridge voltage of the full bridge, where the detected cross-bridge voltage is used to infer the occurrence of the analyte selectively taken up by the receptor layer, preferably the magnitude of the occurrence.

A full bridge voltage detector may in particular be any detector capable of detecting a voltage. For example, this may be a measuring resistor, or a signal transmitter or a measuring device that indicates the voltage, or another type of detector that generates an output signal by detecting a voltage.

The cross-bridge voltage detector may be configured to generate a single output value, such that only the occurrence of a cross-bridge voltage is indicated. In particular, it is possible to infer from the occurrence of a cross-bridge voltage that an analyte in a certain minimum concentration has interacted with the receptor layer of the test cantilever, and as a result the electrical properties of the transducers, or at least the electrical property of the active transducer of the test cantilever, have changed.

However, a cross-bridge voltage detector can also indicate various output values that preferably have a simple functional relationship with the cross-bridge voltage. For example, this may mean that the output value from the cross-bridge voltage detector rises if the cross-bridge voltage rises. However, this may also mean that the output value from the cross-bridge voltage detector drops if the cross-bridge voltage rises. It is particularly advantageous when it is possible to infer an unambiguous value for the cross-bridge voltage from the output value from the detector. In other words, it is preferable for the output value from the cross-bridge voltage detector to follow a bijective function of the cross-bridge voltage.

The change in the bridge voltage is ideally expressed as a ratiometric change in relation to a defined, i.e. measured, supply voltage. For example, a drift in the supply voltage then does not influence the measured signal.

The various output values need not be restricted to the signal amplitude, but rather may be restricted to the temporal occurrence of the output value. For example, the cross-bridge voltage detector may release one pulse per time interval in the case of a first voltage, whereas the cross-bridge voltage detector releases four pulses per time interval in the case of a second voltage. The occurrence of the pulses may thus be used to indicate the strength of the cross-bridge voltage. In particular, the output value may thus be coded.

The electrical properties of the transducers may be output via an A/D converter, and an A/D converter logic unit may be configured to provide a differential measurement and/or an absolute measurement of the bending states.

In particular, the cross-bridge voltage detector may be formed as an A/D converter, where an A/D converter is a converter electronics system that generates a digital signal from an analogue signal. For this purpose, for example, the strength of the measured signal is sampled point by point with a certain periodicity by the A/D converter, and the measured voltage is converted to a digital value.

The A/D converter may in particular comprise an A/D converter logic unit, where the A/D converter logic unit can be put into different modes of operation by adjusting the internal circuitry, in particular through software modifications. The various modes of operation may be used to tap off various voltages (in particular AC voltages and/or DC voltages) and measured signals from the electrode circuit.

For example, the A/D converter may have what is called a differential measurement mode in which only the change in bending state between the reference cantilever and the test cantilever is detected. In this differential measurement mode, in particular, the cross-bridge voltage is tapped off such that a change in the bending states of the cantilevers is detected in the form of occurrence of a cross-bridge voltage. The differential measurement mode is the preferred measurement mode for detecting binding of an analyte to the receptor layer.

However, it is also possible to operate the A/D converter in what is called an absolute measurement mode, in which the individual transducers are accessed directly via the electrodes (single ends mode). This makes it possible to measure the individual transducer resistances, for example for quality assurance purposes, or else in order to characterize the full bridge. In addition, it is possible thereby to detect the absolute bending states of the cantilevers.

Overall, an A/D converter can thus convert the cross-bridge voltage to a digital signal, where the A/D converter can be operated in a differential measurement mode and/or in an absolute measurement mode using an A/D converter logic unit.

In this design in particular, only one A/D converter is required, such that the production process can be implemented inexpensively.

Owing to the stable and balanced full bridge, it is additionally also possible to move the A/D converter far away from the actual transducers and cantilevers, such that waste heat from the A/D converter, for example, does not affect the measurement result.

The sensor may be formed on a chip.

This may mean that the sensor is produced on a semiconductor structure that permits further data processing of the cross-bridge voltage or of the output value from the A/D converter logic unit. In particular, a chip may also mean what is called a system-on-a-chip, wherein all the functional units of the measurement system are formed integrally on a single electronic component.

However, it should be taken into account here that the production process chain for the sensor may comprise gold, which can impair the production of an A/D converter logic unit using CMOS semiconductor techniques.

A multitude of cantilever pairs may be arranged on a chip, in which case an A/D converter logic unit may be configured to provide signal multiplexing of the measured signals.

A cantilever pair in each case comprises a reference cantilever and a test cantilever. A multitude of such cantilever pairs along with active and passive transducers may be arranged on a chip, and each be read in turn by an A/D converter logic unit.

In particular, it may also be the case that a first cantilever pair reacts specifically to a first analyte and a second cantilever pair reacts to a second analyte, such that different analytes can be detected by a sensor.

However, a multitude of cantilever pairs may also comprise a first number of test cantilevers and a second number of reference cantilevers. For example, the various reference cantilevers may detect different interfering influences in a particularly sensitive manner, these together delivering the reference for the number of test cantilevers.

The cantilever pairs can be operated simultaneously using an appropriate A/D converter logic unit. It is thereby possible firstly to detect a large number of different analytes using different receptors and reference layers. Secondly, however, it is also possible to establish a statistical statement as to the significance of the measured cross-bridge voltages through identical receptor layers and reference layers.

The test converter layer and/or reference converter layer on the surfaces of the test and/or reference cantilevers may comprise an activation layer, where the activation layer is configured, in the event of a force acting on the reference and test cantilevers, to provide a greater surface extension compared to the non-activated lower surface of the reference and test cantilever, and where the activation layer, for example, consists of gold.

Activating the upper surface may mean that an adhesion promoter for a further layer is provided by applying an activation layer. The reason for this may be that the base material of the cantilever, for example, does not enter into a bond with a subsequent layer. The subsequent layer may, as described further down, be a function layer.

The activation layer may in particular comprise gold, or consist entirely of gold.

Because the upper surface has an activation layer, the structure of the cantilevers is in particular non-homogenous or asymmetric in terms of height, but rather consists of layers. This can significantly influence the elasticity or stiffness of the cantilever, such that a greater surface extension arises on the upper surface in the event of deformation of the cantilevers, which in turn leads to a larger measured signal.

Owing to good conductivity, the coating of the cantilevers with gold may likewise be used to form electrodes for the transducers. For this reason, the distance between the electrodes may also be minimized, since the smallest possible area of the cantilever is thus not coated with gold. Accordingly, the coated area may be maximized, which results in a particularly high level of deformation.

The activation layer may in particular also consist of a chromium-gold alloy, since this influences the mechanical properties of the cantilever to a lesser degree. The inclusion of chromium in particular achieves homogeneity of the crystallites of the gold layer, such that any disruptive anisotropic effects can be avoided by the crystal lattice of a hypothetical crystalline layer.

The lower surfaces of the reference and test cantilevers may be passivated by a passivation layer, where the passivation layer is configured to minimize non-specific protein adhesion on the reference and test cantilevers, and where the passivation layer comprises trimethoxysilane and/or a blocking substance.

Unlike an activation layer, a passivation layer is a layer intended to minimize or prevent any interaction between the cantilever and another material. Thus, in the production of the receptor layer or reference layer, this binds solely to the upper surface of the cantilever and not to the lower surface of the cantilever. Through binding of the receptor layer or reference layer to the analyte, this can achieve a greater surface tension on the upper surface. This further increases the asymmetry of the layer structure, which can lead to improved extension properties for the signal detection.

Suitable materials for the passivation of the lower surface are in particular trimethoxysilane, and what are called blocking layers. This passivation layer minimizes what is called non-specific protein adhesion. Protein adhesion is adhesion of a protein to the surface. Non-specific adhesion of a protein or of a substance in general to the cantilever may lead to distortion of the measurement result, since these non-specific substances likewise interact with the cantilevers. By preventing this non-specific adhesion, the relative influence of the intended specific adhesion or interaction of the analyte with the cantilever relative to the basic state of the cantilever is increased.

However, it is also possible for a passivation layer also to bind the analyte, but in such a way that the resulting surface tension is the opposite of the surface tension of the activation layer. This makes it possible to achieve greater deformation of the cantilevers.

The so-called blocking layer may in particular be adapted to the respective analyte under investigation, in order to define a measurement window for the analyte. The blocking layer is applied here in what is called the spotting process or washing process.

In the washing process, a so-called "sealer" protects the hydrate envelope of the detector proteins during drying and thus makes them storable. The sealer is incorporated in a matrix in soluble form, such that it is soluble for a sample liquid such as water. The sealer additionally has a certain layer thickness, such that the cantilevers are mechanically stabilized, which increases protection during storage of the cantilevers. A sealer may for example contain sugar. Sugar crystals are hydrophilic and therefore protect the hydrate envelope of the proteins. What is called reconstitution of the proteins, in which the dried proteins are reactivated in the measurement liquid, is thus possible.

In the case of spotting of the receptor proteins, so-called "buffers" are used in order to enable reconstitution of the proteins in the sample liquid. Here too, the storability of the sensors is increased by drying.

The active and the passive cantilevers may be of chemically identical structure.

For this purpose, the reference cantilever and the test cantilever have an identical layer structure that differs only in that a receptor layer has been applied to the test cantilever and a reference layer to the reference cantilever. In particular, chemical identity thus means that the two cantilevers differ only in the reference/test layer.

This is achieved in that the measured signal, in particular in the case of a differential measurement of cross-bridge voltage, is based solely on the influence of the analyte on the cantilevers and is not caused by further properties of the cantilevers.

In particular, chemical identity means that the cantilevers are changed and adapted to the extent that they differ only in terms of their binding properties or interaction properties with respect to the analyte to be analysed. For all further substances, the intention is to achieve very substantially identical interaction, or minimum interaction.

Overall, the overall layer structure of the cantilevers described above can also be inverted. This means that the reference and receptor layers, rather than being applied to the upper surface, may also be applied to the lower surface of the cantilevers. For example, the receptor layer may also be arranged on the bottom side of the cantilever.

In order for the cantilever to deform, any chemical binding to the cantilever should ideally take place on one side. When the analyte binds to the upper side, there should not be any non-specific binding to the lower side of the cantilever, since otherwise the surface tension that results from the chemical binding of the analyte may be compensated for by the non-specific chemical binding to the lower side of the cantilever.

In other words, the chemical binding to the top side and the bottom side must be at least asymmetric in order to achieve a deformation. Stronger binding to the top side than to the bottom side or stronger binding to the bottom side than to the top side accordingly leads to a measurable deformation of the test cantilever.

The receptor layer may comprise antibodies for an antigen and the reference layer may comprise an antigen-specific isotype control antibody targeting the antibody of the reference layer.

Antibodies are proteins that are produced by body cells as a reaction product to antigens. Antibodies are typically used by the human immune system to bind to the antigens of viruses, for example, such that the viruses are marked and an outbreak of a viral infection can be avoided by the immune system. It may in particular be the case that an antibody binds to different antigens, such that the specificity of the antibody is lowered. There are also antibodies that bind to non-immunological targets, for example THC.

By contrast, an isotype control antibody specifically does not bind to the antigen of a virus, such that, in the event that there is simultaneously binding of the antibody to the antigen and of a non-binding isotype control antibody to the antigen with high specificity, the presence of a particular virus or antigen of a virus may be inferred.

The antibody of an antigen may be part of the receptor layer of the test cantilever, while the isotype control antibody of the antigen may be part of the reference layer. This has the advantage that deflection of the test cantilever can be confirmed simultaneously by non-deflection of the reference cantilever.

In other words, a passivation layer may be applied to the lower surfaces of the reference and test cantilevers, an activation layer may be applied to the upper surfaces of the reference and test cantilevers, the reference and test function layer, preferably with a self-assembly monolayer, may preferably be applied to the activation layer, and a reference layer or receptor layer may preferably be applied to the self-assembly monolayer of the reference or test cantilever, where the receptor layer comprises antibodies for an antigen and the reference layer comprises an antigen-specific isotype control antibody targeting the antibody of the receptor layer.

The layers may be produced in a dipping/spotting process, where the spotting may preferably be performed by means of commercially available machines. Droplets of the respective layer are deposited here on the cantilever, so as to spatially delimit the functionalization, which in particular enables inexpensive and independent coating of the cantilevers. The very small drops are prevented from drying by suitably controlling the environmental parameters, such as temperature, air humidity and dew point. The lower sides of the cantilevers are not activated here, and so the antibodies used come into contact solely with the upper surface of the cantilever. The layers are then dried, such that a higher or lower temperature has little or preferably no influence on the antibodies. This allows a long shelf life, in particular in an inert gas. The protein layers are in particular applied after the function layers have been applied, but before the sensors are singularized from the wafer.

The receptor layer may comprise, for example, Sars-CoV2 antibodies and the reference layer may comprise Sars-CoV2-specific isotype control antibodies. The Sars-CoV2 antibody binds preferentially to the Si or N antigen of the Sars-CoV2 virus. The antibody is monoclonal, and has high sequence fidelity and specificity with respect to the Sars-CoV2 antigen. In particular, the antibody may be produced via what is called the phage display method. The Sars-CoV2-specific isotype protocol antibody on the other hand may have ultrahigh specificity with respect to the corresponding antigen, but otherwise be identical to the active antibody.

This enables, for example, rapid detection of the Sars-CoV2 virus. In particular, the electrical measurement and the accumulation of the antibodies on the test cantilever gives a rapid test method that additionally has high specificity through the comparison with the lack of accumulation on the reference cantilever.

The receptor layer can generally provide molecule-specific binding forces, and the reference layer provides no molecule-specific binding forces. It is thereby possible to detect a particular molecular species.

The receptor layer may comprise single-strand DNA (ssDNA) and/or other DNA fragments that are able to bind specifically to DNA fragments in the sample. The reference layer may comprise single-strand DNA and/or other DNA fragments that do not bind to chemical and/or biochemical and/or physical species in the sample, but correspond to the receptor layer in terms of characteristic parameters (for example chain length, chemical structure).

The receptor layer may comprise single-strand RNA and/or other RNA fragments that are able to bind specifically to RNA fragments in the sample. The reference layer may comprise single-strand RNA and/or other RNA fragments that do not bind to chemical and/or biochemical and/or physical species in the sample, but correspond to the receptor layer in terms of characteristic parameters (for example chain length, chemical structure). It is thereby possible to detect a particular DNA or RNA and their fragments and/or other oligonucleotides.

The receptor layer may comprise antibodies and/or other and/or further proteins that are able to specifically bind target proteins, and the reference layer may accordingly comprise specific isotype control antibodies and/or further proteins that do not bind to chemical and/or biochemical and/or physical species in the sample.

The receptor layer may comprise scFv antibody fragments and the reference layer may comprise scFv antibody fragment-specific isotype control antibodies. An scFv antibody is an artificially produced antibody fragment. Because an antibody can be broken down into multiple fragments, the reactivity of the sensor to a low sample concentration may be increased.

The receptor layer and the reference layer may comprise hydrogels.

Hydrogels are molecular matrices that have very good ability to bind water and swell up significantly on contact with water. By chemically modifying the hydrogels, in particular the matrix, it is possible to bring about a strong reaction of the hydrogel to the presence of proteins or other analytes, such that the mechanical deformation of the cantilever is multiplied. In particular, it is thus also possible to perform a pH-sensitive measurement of the analyte.

BRIEF DESCRIPTION OF THE DRAWING

Exemplary embodiments of the invention are elucidated in detail by way of the description of the figures that follows. The figures show:

FIG. 9A is a schematic diagram of selected layers of a cantilever without function layer, with neutral axis drawn in;

DETAILED DESCRIPTION

Figure 1:
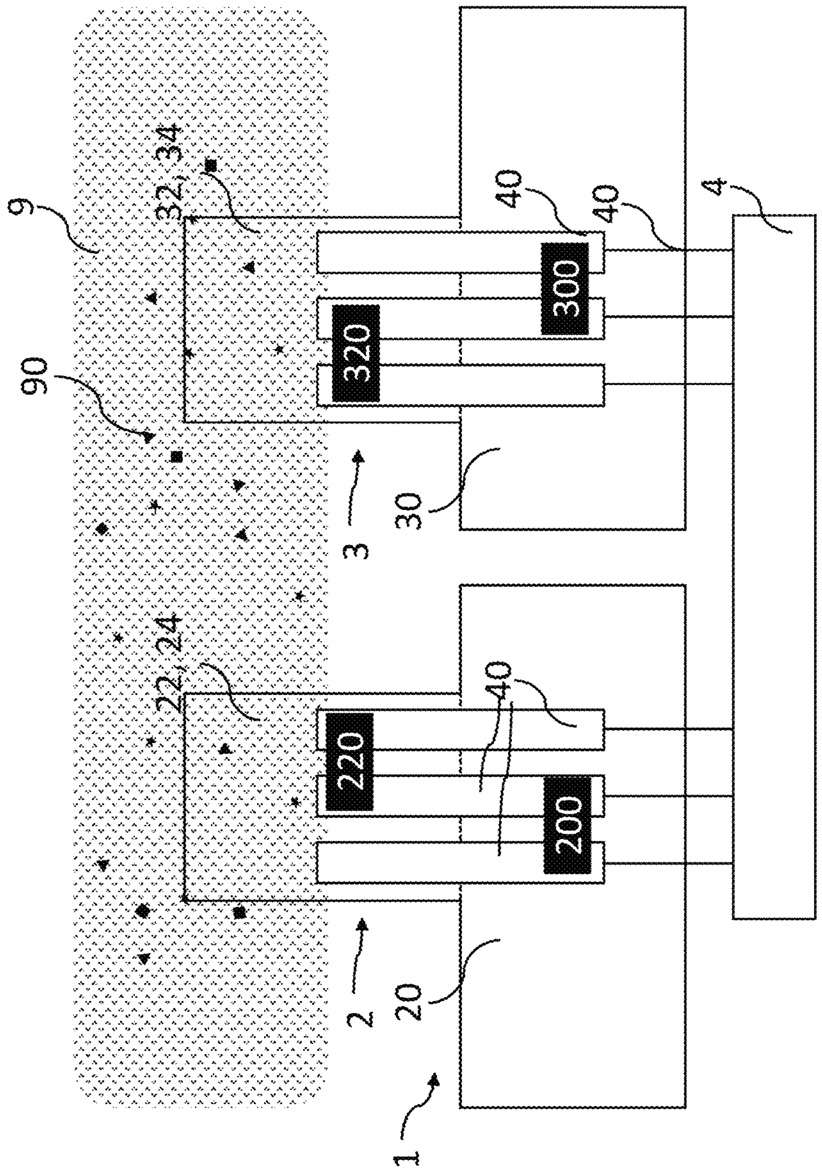
FIG. 1 is a schematic diagram of a first embodiment of the sensor.

Exemplary embodiments are described below with reference to the figures. Elements that are identical, similar or have the same effect are given the same reference numerals here in the various figures, and repeated description of these elements is omitted in some cases in order to prevent redundancy.

FIG. 1 shows a schematic of a first embodiment of the proposed sensor 1 for converting chemical and/or biochemical information. The sensor 1 comprises a test cantilever 2, which in turn has a base 20, and a deformable part 22. A passive test transducer 200 is arranged on the base 20, while an active test transducer 220 is arranged on the deformable part 22.

In a similar manner, the sensor 1 also has a reference cantilever 3, which in turn has a base 30 with a passive reference transducer 300, and a deformable part 32 that has an active reference transducer 320.

The transducers 200, 220, 300, 320 are each connected, via electrodes 40, to electronics 4 that are capable of recording or of forwarding a measured signal from the transducers 200, 220, 300, 320, while the electronics 4 are likewise capable of supplying the transducers 200, 220, 300, 320 with current and/or voltage.

The sensor 1 has the objective of indicating the occurrence and/or the concentration and/or the amount of an analyte 90 in a sample 9.

In FIG. 1, the sample 9 is a fluid that has been produced, for example by treatment of a swab, in particular a nose swab or a throat swab, from a test subject. However, it may also be the case that the sample 9 is saliva or blood or another bodily fluid. However, it may also be the case that the sample 9 is a gargling fluid that the test subject has gargled. It may also be the case that the sample 9 has been obtained and/or synthesized from a tissue sample or another substance taken from the test subject. The analyte 90 may be dissolved here in the sample, or be in undissolved form, as a suspension or dispersion or emulsion.

In any case, the sensor 1 should be used to examine the sample 9 for the occurrence and/or a concentration and/or an amount of an analyte 90 in the sample 9. For this purpose, a receptor layer 24 is applied to the test cantilever 2, with which an analyte 90 can interact, or a receptor layer 24 that can adsorb or absorb the analyte 90. In the case of adsorption, the analyte 90 would adhere to the surface of the receptor layer 24, while in the case of absorption the analyte 90 would penetrate into the interior of the reference layer 90.

If the sample 9 includes an analyte 90, this analyte may thus interact with the receptor layer 24. This can have the effect that there is a change in the surface tension of the section coated with the receptor layer 24 in the deformable part 22 of the test cantilever 2. This change in surface tension can be registered by the active test transducer 220, which is in turn interpreted in the electronics 4 as the measured signal.

This change in the surface tension of the section coated with the receptor layer 24 in the deformable part 22 of the test cantilever 2 can also lead to deformation of the deformable part 22 of the test cantilever 2. The active test transducer 220 can therefore also register a deformation of the deformable part of the test cantilever 2, which is in turn interpreted in the electronics 4 as the measured signal.

However, a force exerted by the active test transducer 220 may already be registered owing to the interaction with the sample fluid 9, for example in that merely the surface tension of the fluid acts on the deformable part 22 of the test cantilever 2. Accordingly, in this case, it is not the presence of an analyte 90 that is responsible for a correspondingly resulting the formation or change in surface tension.

In order to establish the magnitude of this basic effect of the sample 9 on the test cantilever 2, the reference cantilever 3 is also brought into contact with the sample 9 at the same time as the test cantilever 2. For this purpose, the reference cantilever 3 has a reference layer 34, with which an analyte 90 cannot interact, or a reference layer 24 that is not able to adsorb or absorb the analyte 90. In this case, any interaction with the analyte 90 should be avoided in order to enable differentiation with regard to the measured signal from the test cantilever 2.

Since both the test cantilever 2 and the reference cantilever 3 interact with the sample 9, both cantilevers 2, 3 interact similarly with the sample 9. The difference in this case is however that the test cantilever 2 is additionally able to interact with any analyte 90 present via its reference layer 24. Accordingly, the measured signals from the active transducers 220, 320 differ, if an analyte 90 occurs in the sample 9. The magnitude of the difference between the measured signals can accordingly, in the simplest case, be used to infer the amount of the occurrence of the analyte 90 in the sample 9.

However, the test cantilever 2 and the reference cantilever 3 measure the occurrence of the analyte 19 in the sample 9 at different positions. There may be different environmental conditions at different positions of the sample, for example fluctuations in temperature or concentration gradients, etc. These different environmental conditions may be measured by the passive transducers 200, 300.

The passive transducers 200, 300 are arranged on the base and preferably do not detect any measured signal in the event of a deformation or change in the surface tension of the deformable part 22, 32 of the reference or test cantilevers 2, 3. However, the base level of the measured signal from the passive transducers 200, 300 may be influenced due to these different environmental conditions. Because the passive transducers 200, 301 provide a comparison value for each measured value from the active transducers 220, 23 that gives a view of the environmental conditions in isolation, the influence of the environmental conditions on the measured signals from the active transducers 220, 320 may be determined and reduced, or factored out or isolated.

The sensor 1 can accordingly be used to analyse the occurrence of an analyte 90 in a sample 9 in isolation, since due to a multitude of measurement points on the reference and test cantilevers 3, 2 the influence of interactions that are not associated with the analyte 90 is reduced and isolated. This enables high measurement accuracy of the occurrence of the analyte 90 in the sample 9.

Figures 2A, 2B:
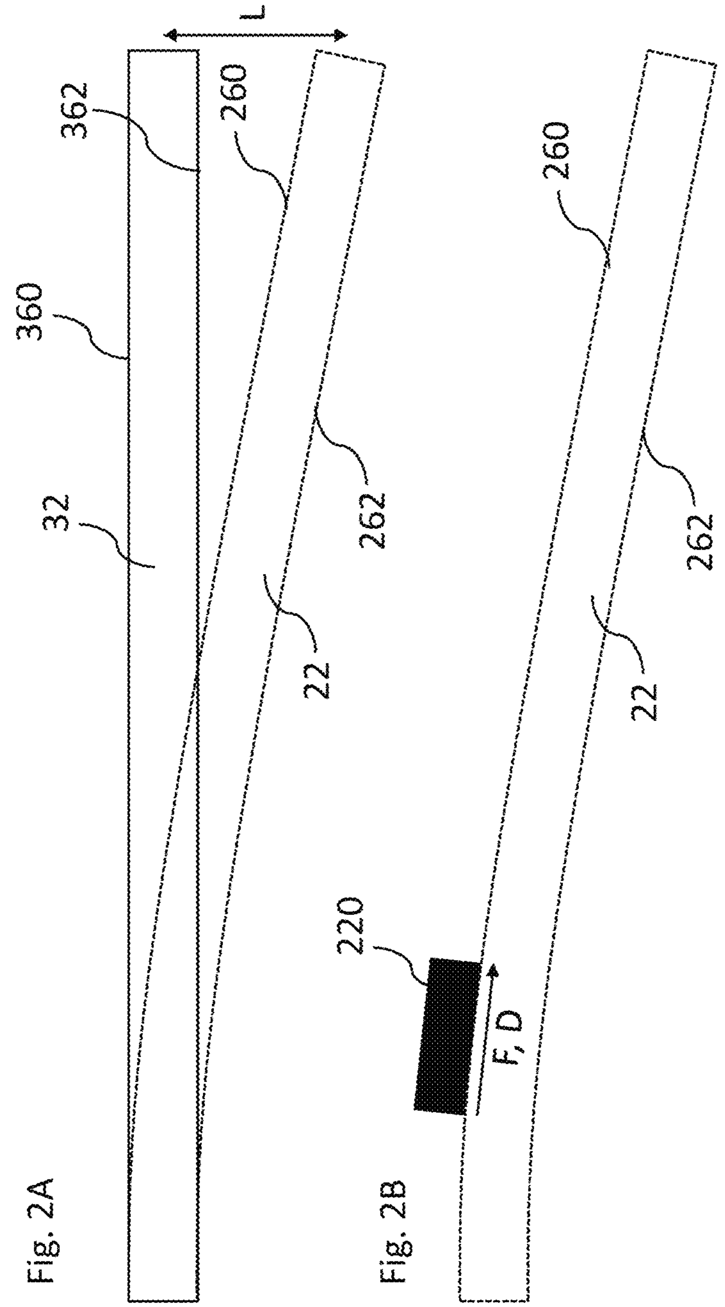
FIGS. 2A, 2B, 2C and 2D are schematic diagrams of the cantilevers.

FIG. 2A shows the comparison of the deformable parts 32, 22 of the reference and test cantilevers 3, 2 in the event of a deformation and longitudinal extension. The deformable part 32 of the reference cantilever 3 has an upper surface 360 and a lower surface 362. The deformable part 22 of the test cantilever 2 likewise has an upper surface 262 and a lower surface 262. If an analyte 90 in the sample 9 interacts with the test cantilever 2, or with the receptor layer 24, there is a change in surface tension and, for example, deformation of the deformable part 22 from the stationary part (that merges into the base of the test cantilever) toward the freely mobile part of the deformable part 22. The deflection L shown here results from the relative deflection between the deformable part 32 of the reference cantilever 3 and the deformable part 22 of the test cantilever 2 due to the interaction with the analyte 90.

The deformation of the deformable part 22 of the test cantilever 2 is shown in FIG. 2B. The cause of this is that the upper surface 260 and the lower surface 262 extend to different degrees. Because of the large extension D on the upper surface 260, an active transducer 220 applied thereto may register a change in surface tension and/or an extension force F. The registered change in surface tension and/or the extension force F may be converted here to an electronic signal by the active transducer 220 or influence an existing electronic signal, for example an applied voltage. This can be accomplished, for example, in that the resistance of the transducer changes if it experiences an extension force F, which in turn results in an extension of the transducer 220.

The transducer would also be able to detect a contraction of the surface on which it is arranged. In the embodiments disclosed, however, the transducers are always arranged on surfaces where an extension is expected.

However, the extension and/or change in surface tension and/or force detected by the transducer may also be a bending force or a shear force, or be brought about by a bending force or shear force, or generally be based on the modulus of elasticity of the respective cantilever. In particular, the attachment of the deformable part 22, 32 to the base 20, 30 has the result that the deformable part 22, 32 becomes aligned along a bending curve due to a force exerted by a change in the surface tension of the test cantilever. The resulting bending curve results in particular from the geometry, in particular the surface moment of inertia, of the cantilever, and by the mass of the cantilever and the modulus of elasticity. The bending curves may be described, for example, in accordance with beam theory.

The different surface tensions on the lower side and the upper side of the cantilever accordingly result in the described deformation or extension of the cantilever.

Beam theory makes it possible, for example, to predict the point on the deformable part 22, 32 at which the extension D will be at its greatest. It is possible to arrange the active transducer 220, 320 at this point in order to achieve an optimum signal-to-noise ratio and in order to have maximum sensitivity to the extensions. In the exact positioning of the transducers, however, other boundary conditions should also be taken into account.

Figure 2C:
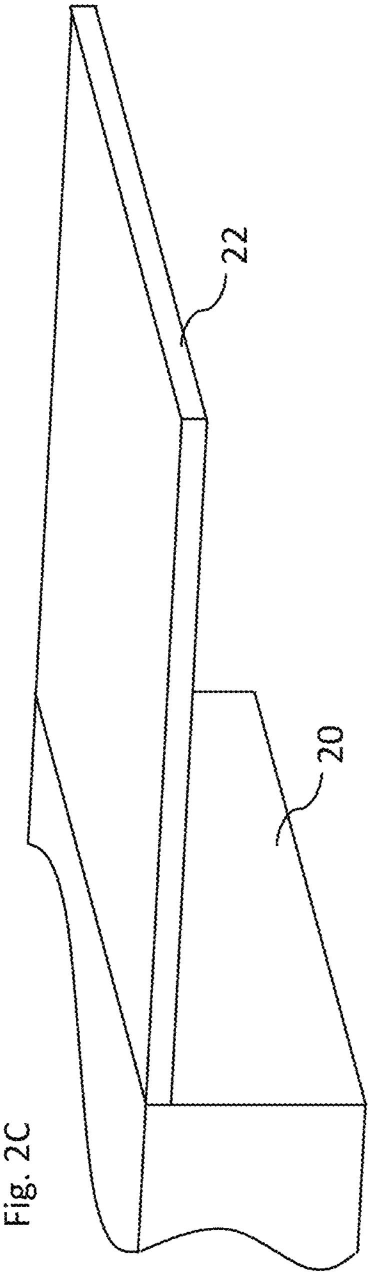
Figure 2D:
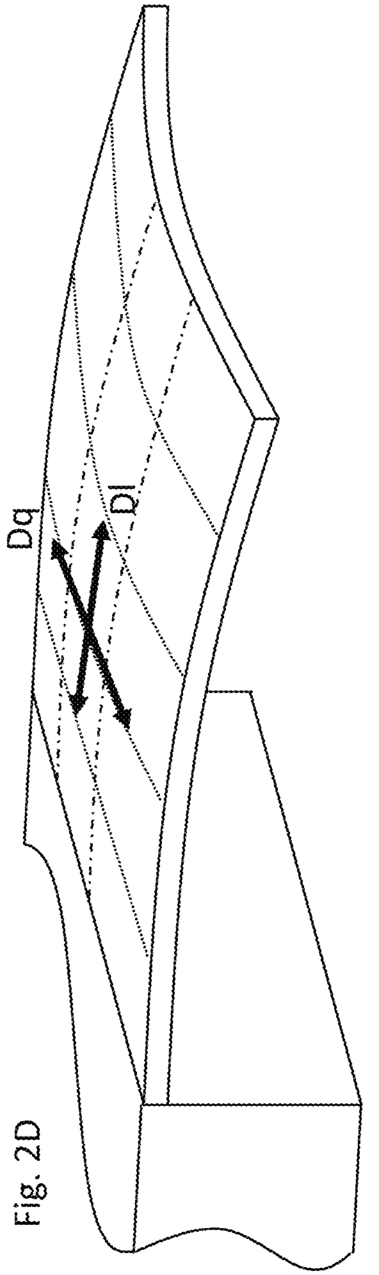

In particular, the alignment of the transducers relative to the alignment of the cantilevers plays an important role. For example, FIG. 2C shows a non-deflected cantilever. If the cantilever comes into contact with the analyte, the surface tension changes and there is deformation of the material, as shown in FIG. 2D. FIG. 2D illustrates that the cantilever undergoes deformation perpendicular to the base 20, or to the bending edge. This is accompanied by a longitudinal extension DI of the upper surface. At the same time, deformation takes place parallel to the base 20, or to the bending edge, which is accompanied by a transverse extension Dq of the upper surface. The geometry of the cantilever makes it possible to determine the direction in which a greater extension D is brought about. The transducer may in particular be aligned in this direction in order to generate a particularly large measured signal.

By virtue of an increased mechanical extension at the site of the transducer, it is possible to even further improve the signal found by the transducer. Such an increased mechanical extension can be achieved, for example, via the arrangement and shape of the electrodes.

Figure 3A:
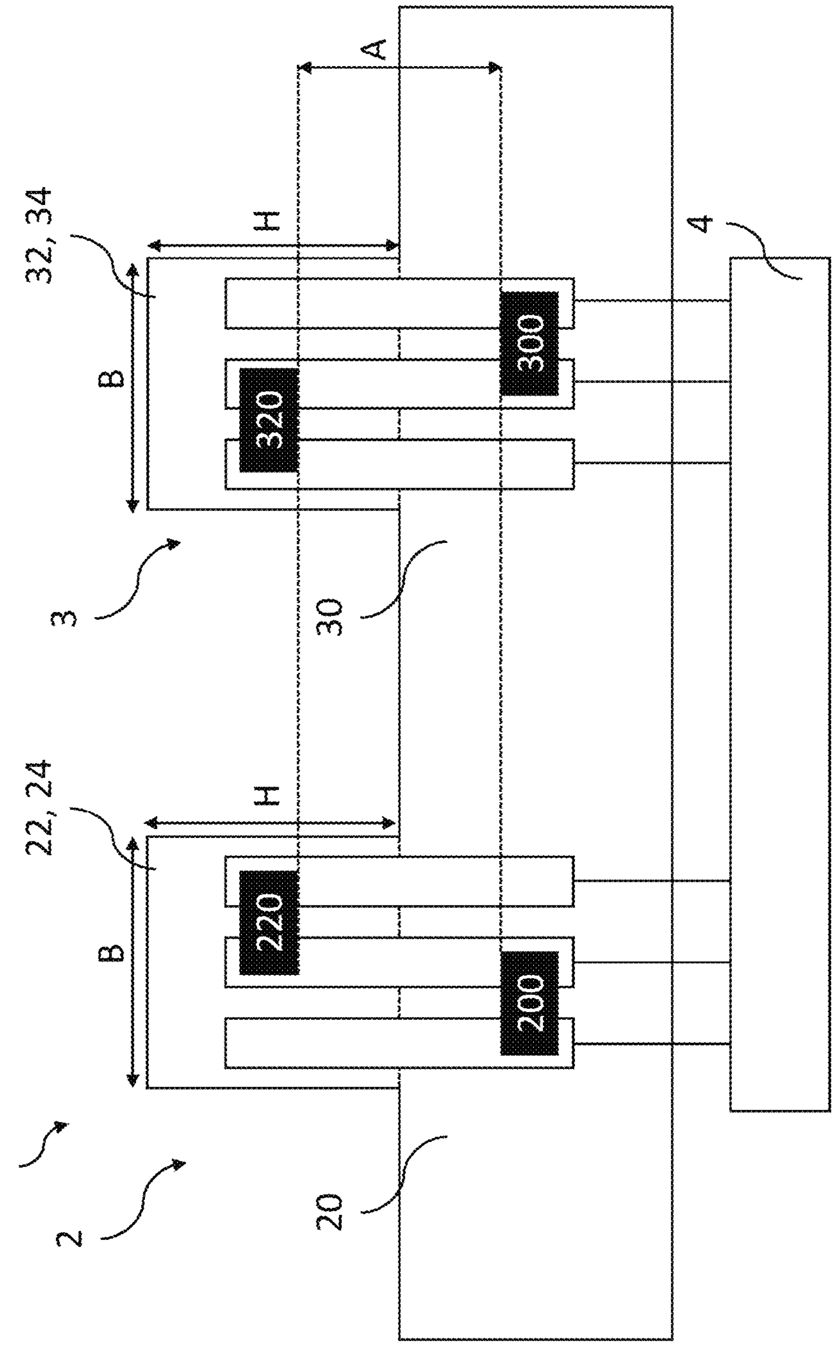
FIGS. 3A and 3B are schematic diagrams of a second embodiment of the sensor.

FIG. 3A shows a further embodiment of the sensor 1. In particular, the reference cantilever 3 and the test cantilever 2 have identical geometric dimensions; in particular, the height, width and thickness of the reference cantilever 3 correspond to the height, width and thickness of the test cantilever 2. This generates an extension D on the upper surfaces 260, 360. Because the geometrical dimensions of the cantilevers 2, 3 are identical, an identical dependence of the measured signal on the extension is accordingly also expected.

The width B of the cantilevers is preferably equal to the height H of the cantilevers 2, 3, thereby allowing a particularly large extension D on the upper surface 260, 360 of the cantilever 2, 3. For example, the cantilevers here have a width of less than 100 μm, a length of less than 100 μm and a thickness of less than 1 μm, in particular a width of 50 μm, a length of 50 μm long and a thickness of 0.3 μm.

In the embodiments of the sensor 1 in FIG. 3, the bases 30, 20 of the reference and test cantilever 3, 2 are additionally arranged on the same overall base. There is accordingly a direct mechanical connection and interaction of the cantilevers via the overall base. This enables, for example, to reduce the different environmental influences on the cantilevers 22, 3, since the cantilevers 2, 3 can be arranged closer to one another. In particular, the bases 30, 20 of the reference and test cantilevers 3, 2 can also be formed as one piece. This ensures that the bases also have the same material-specific binding properties, such that the measurement results from the passive and active transducers 200, 220, 300, 320 have good comparability with one another.

The distance A between the active transducers 320, 220 and the passive transducers 300, 200 is measured in the height direction H of the cantilevers. The distance A is in particular less than 100 μm, thereby ensuring that the transducers are arranged as close as possible to one another, such that, for example, spatial environmental influences on the transducers are reduced.

Figure 3B:
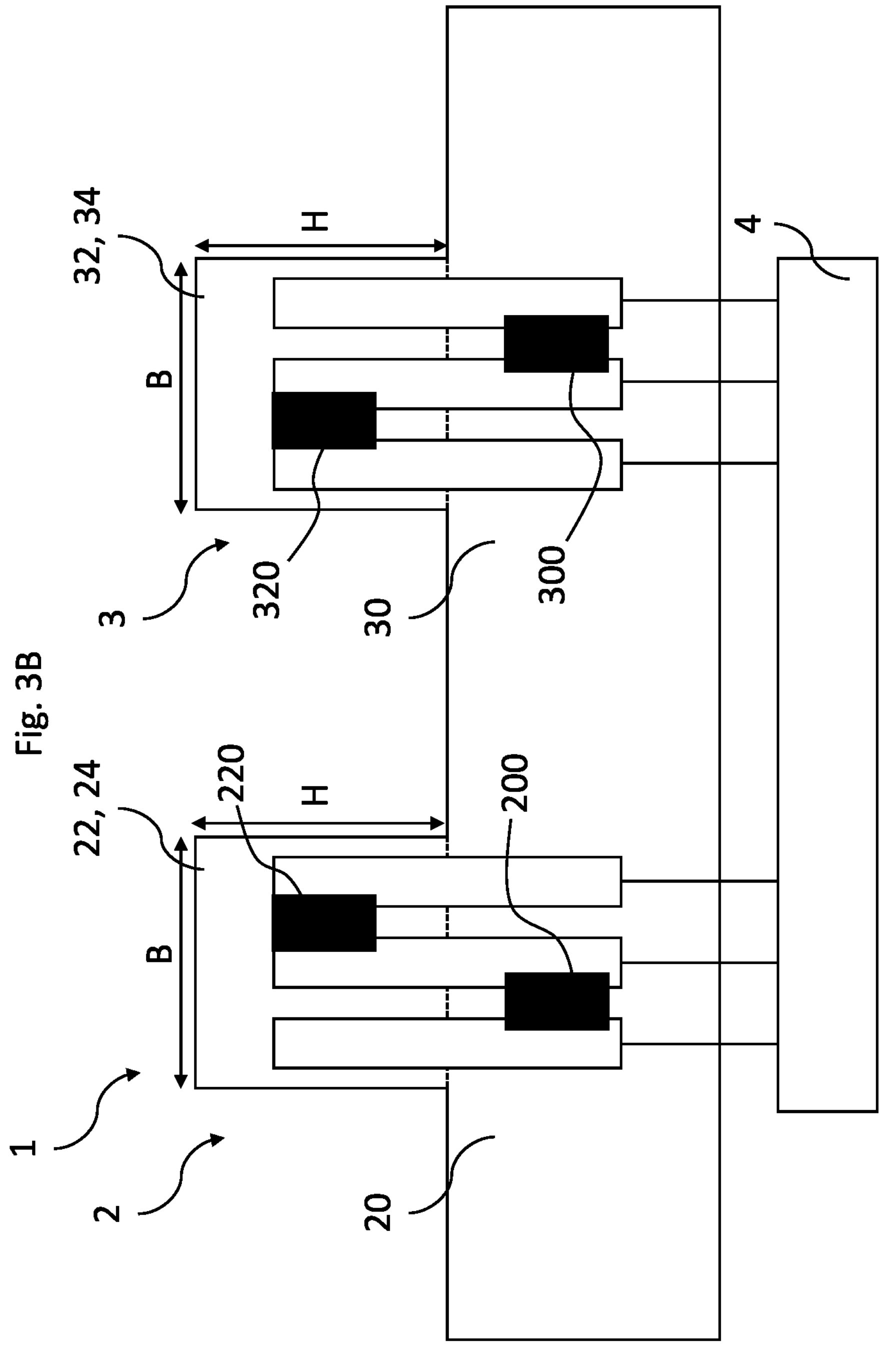

FIG. 3B shows a further embodiment in which the transducers 200, 220, 300 and 320 are aligned perpendicular to the base 20, 30. While a transverse extension of the cantilevers 22, 23 is measured along the bending edge in FIG. 3A with the transverse alignment of the transducers, a longitudinal extension of the cantilevers 22, 23 is measured in FIG. 3B.

Figure 4:
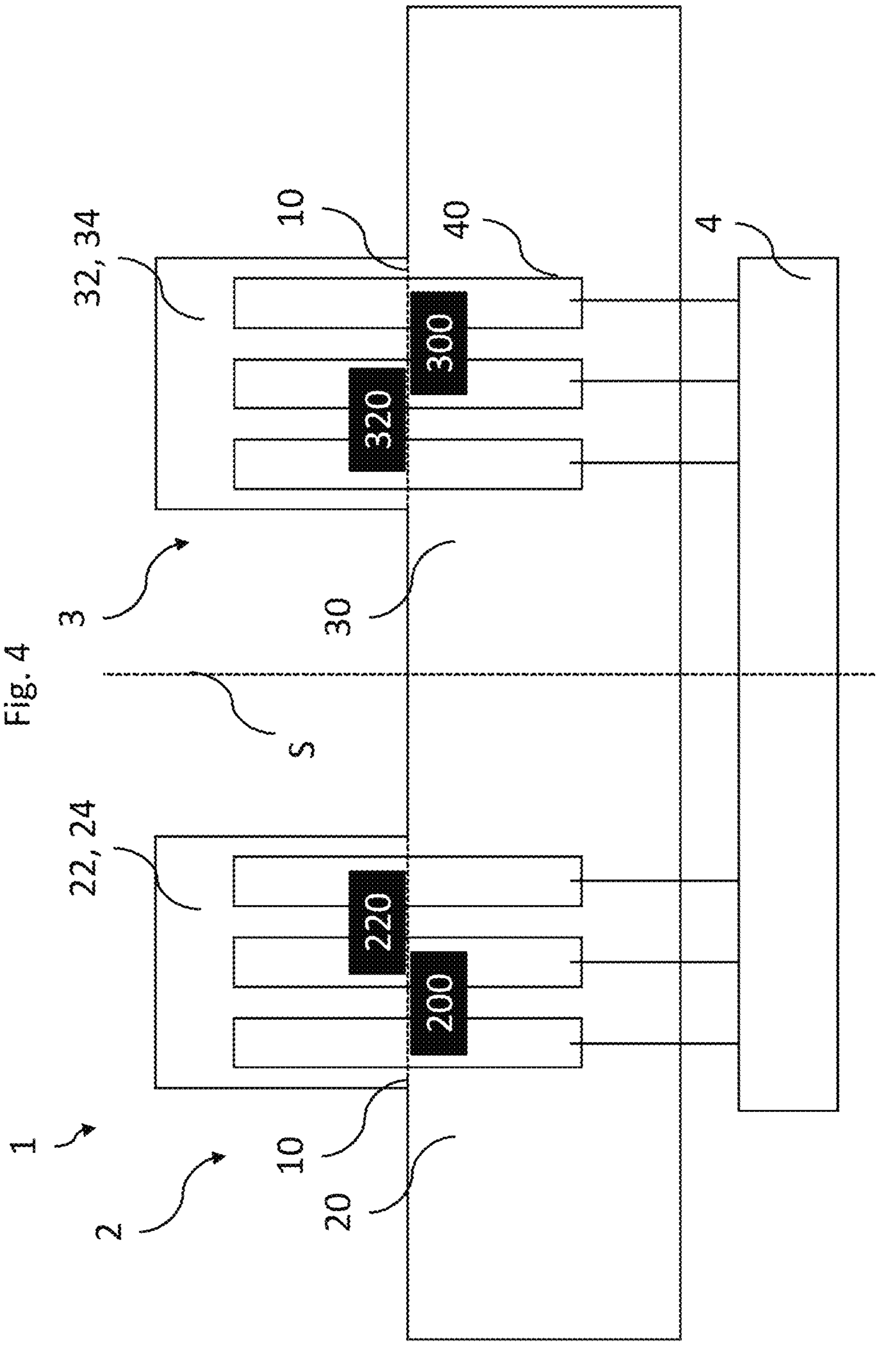
FIG. 4 is a schematic diagram of a third embodiment of the sensor.

FIG. 4 shows one preferred embodiment in this regard, in which the active transducers 320, 220 and the passive transducers 300, 200 each adjoin the bending edge 10 of the cantilevers 3, 2. Since all the transducers 320, 300, 220, 200 adjoin the bending edge 10, the smallest possible distance A between the transducers 320, 300, 220, 200 is achieved. Furthermore, in this embodiment, the electrodes 40 and the transducers 320, 300, 220, 200 have mirror-symmetric orientation with a mirror axis of symmetry S. In particular, the transducers 320, 300, 220, 200 thus have mirror-symmetric orientation relative to one another.

Figure 5A:
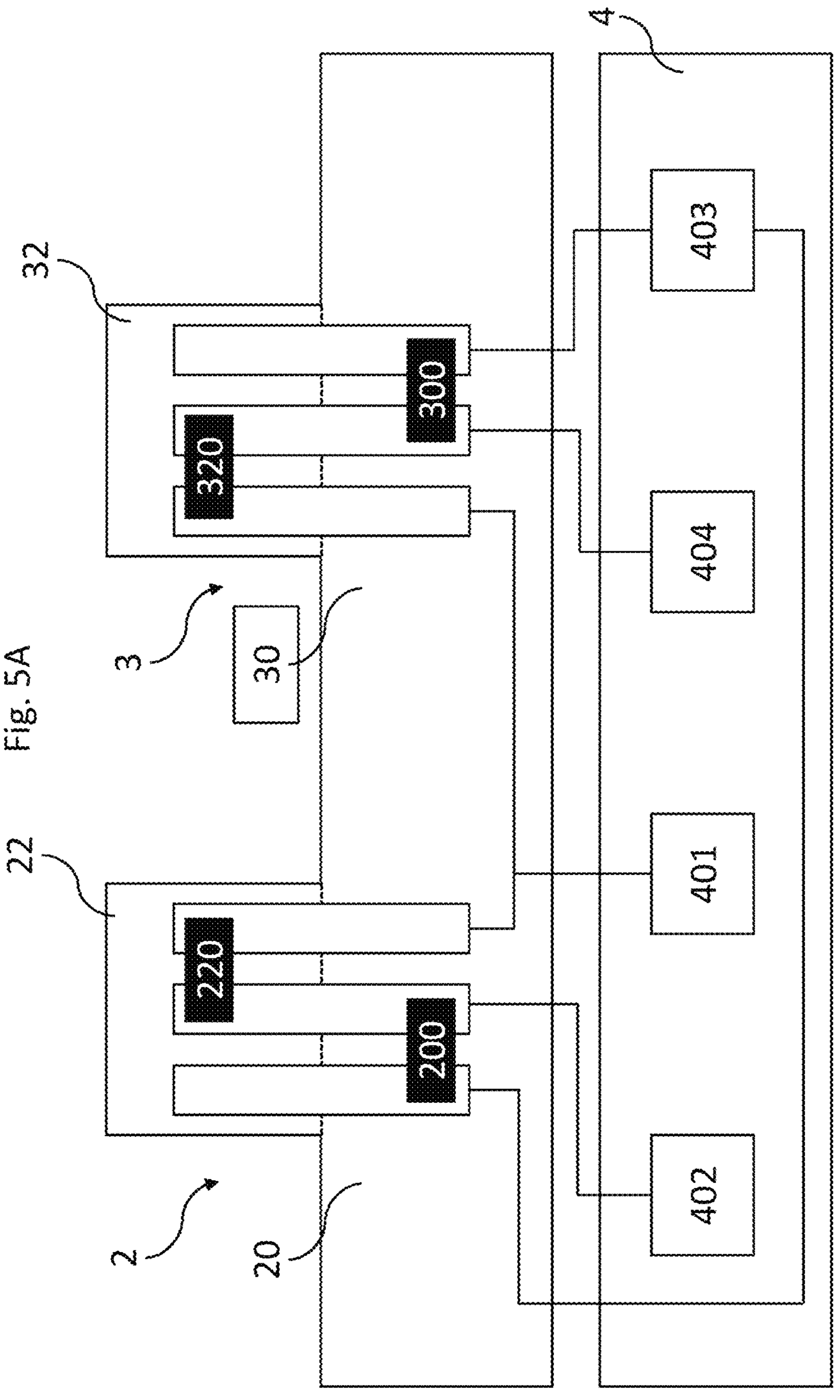
FIGS. 5A, 5B, and 5C are schematic diagrams of additional embodiments of the sensor, and a circuit diagram of a full bridge.

FIG. 5A shows a further embodiment of the sensor 1. The transducers 300, 320, 200, 220 are contact-connected via the electrodes 401, 402, 403, 404. In particular, the active transducer 220 is connected to the active transducer 320 via the electrode 401. In addition, the passive transducer 200 is connected to the passive transducer 300 via the electrode 403. The active transducer 220 is additionally connected to the passive transducer 200 via the electrode 402, while the active transducer 320 is connected to the passive transducer 300 via the electrode 404. The result is thus a total of four electrodes via which the transducers are electrically contact-connected to one another. An electrical contact connection may especially be achieved here in that the transducers are applied to the electrodes so as to establish a conductive connection. Since the transducers have a thickness, it may in particular be the case that, when electrodes are applied subsequently, no conductive contact connection to the electrodes would be achievable at the edges of the transducers. This is ensured only when the thickness of the electrodes is greater than the thickness of the transducers.

Figure 5B:
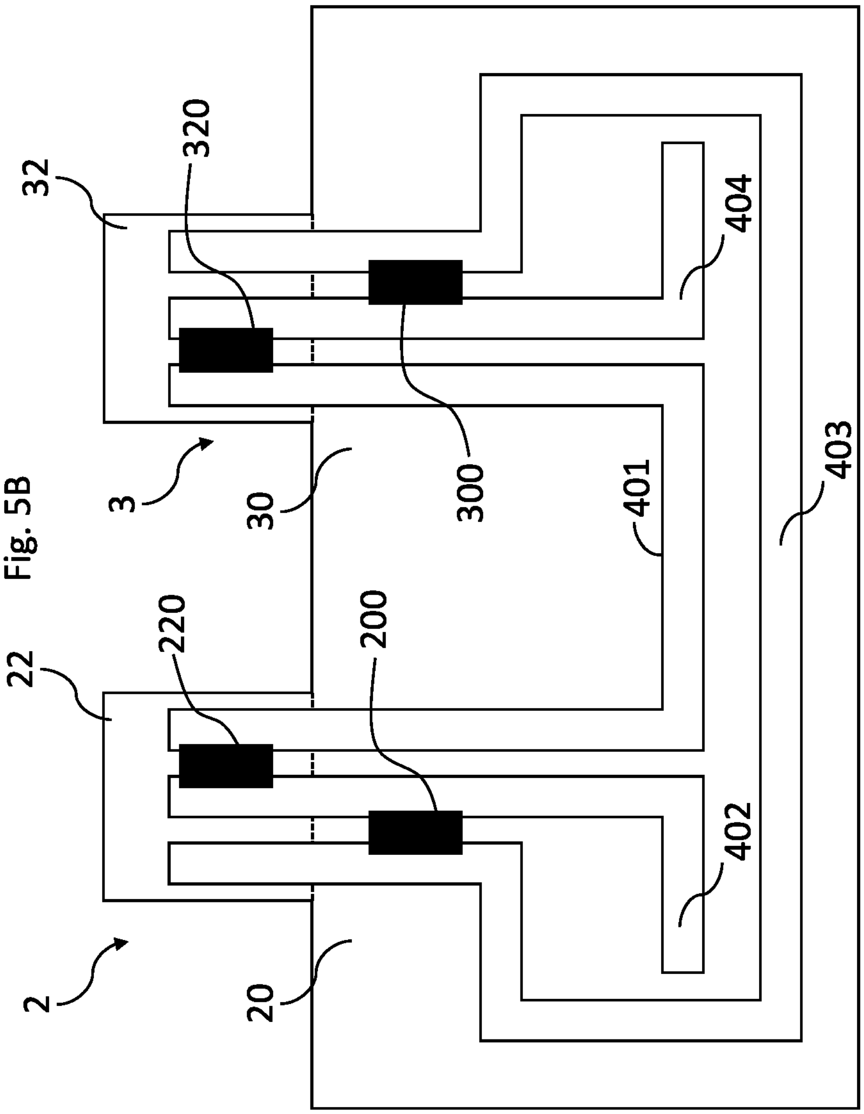

FIG. 5B shows a further embodiment of the sensor 1. The electrodes that contact-connect the transducers 200, 220, 300, 320 have an overall mirror-symmetric structure. Currents flow through the electrodes, or there are voltages across them, such that, when these electrodes have an asymmetric design, there may be asymmetric crosstalk of electrical signals to the other electrodes. This mutual influencing may lead to the generation of a control signal between the electrodes, but this can be avoided by the symmetrical structure.

Figure 5C:
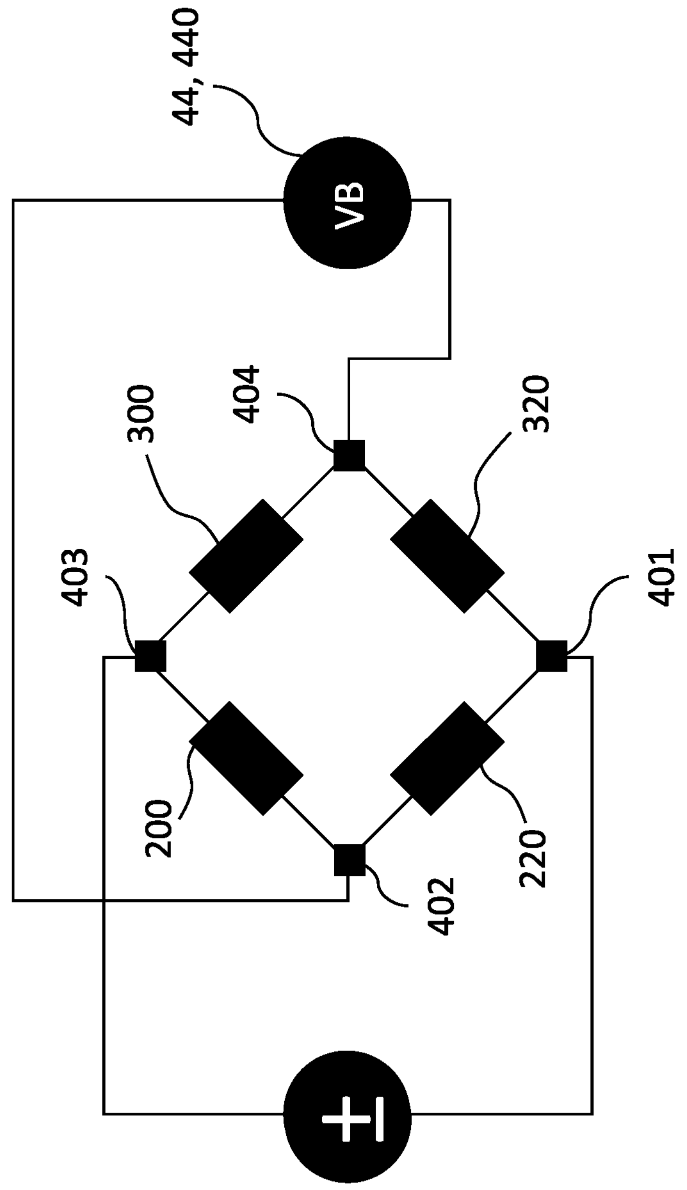

The transducers 200, 220, 300, 320 are in particular electrically interconnected in what is called a full bridge. The circuit of the full bridge is shown in FIG. 5C. In the full bridge, a DC voltage or AC voltage is applied between the electrodes 403, 401. The passive and active transducers act as a voltage divider between these electrodes due to their electrical resistances. A full bridge in the form shown has the advantage that no voltage is established between the electrodes 402, 404 if the ratio of the resistances of the passive transducer 200 to the active transducer 220 of the test cantilever 2 is identical to the ratio of the resistances of the passive transducer 300 to the active transducer 320 of the reference cantilever 3. The deviation of one resistance is in particular sufficient to change the resistance ratios, and thus in order to establish a voltage between the electrodes 402, 404.

When the reference cantilever 3 and the test cantilever 2 interact with the sample 9 and the analyte 90, both deformable parts 22, 32, for example, experience a change in surface tension, which is greater for the deformable part 22 of the test cantilever 2 than for the deformable part 32 of the reference cantilever 3. The resistance of the active test transducer 220 of the deformable part 22 of the test cantilever 2 will accordingly vary to a greater extent than for the reference transducer 320 of the deformable part 32 of the reference cantilever 3. If the resistances of the passive transducers 200, 300 do not change or at least change identically, a change in the resistance ratios results from the deformation of the deformable part 22 of the test cantilever 2 due to the interaction with the analyte 90 in the sample 9, which interacts specifically with the reference layer 24 of the test cantilever 2. In the event of such an interaction, a voltage is accordingly established between the electrodes 402, 404, such that a force exerted on the active test transducer 220 relative to the active reference transducer 320 can be indicated in the form of a cross-bridge voltage VB. The cross-bridge voltage VB is preferably proportional to the occurrence of the analyte 90 in the sample 9, thereby enabling a quantitative assessment of the measured signal.

A cross-bridge voltage detector 44 can indicate the cross-bridge voltage VB externally or forward it, such that the existence of a cross-bridge voltage VB is made visible to the user of the sensor 1. In particular, such a cross-bridge voltage detector 44 may also be formed by an A/D converter, where the A/D converter converts the cross-bridge voltage VB to a digital signal that can be forwarded to an external measuring device. In particular, the A/D converter may be operated in two different measurement modes. The first measurement mode is the differential measurement mode, in which the cross-bridge voltage VB is measured and a relative measured value for the deformation of the two reference and test cantilevers 3, 2 is thus generated. In this differential measurement mode, the measured signals from all the transducers 200, 22, 300, 23 are taken into account, such that the output signal from the A/D converter is a measured signal corrected for environmental influences, which can be used to infer the relative deformation of the deformable parts 32, 22 and thus the occurrence of an analyte 90.

The second measurement mode is the so-called the absolute measurement mode. In the absolute measurement mode, the cross-bridge voltage is not detected; instead, the signals at the electrodes 402 and 404 are tapped off in an isolated manner, such that it is possible to draw a conclusion as to the respective deflections of the deformable parts 32, 22. This information remains unavailable to the user in the differential measurement mode.

Figure 6:
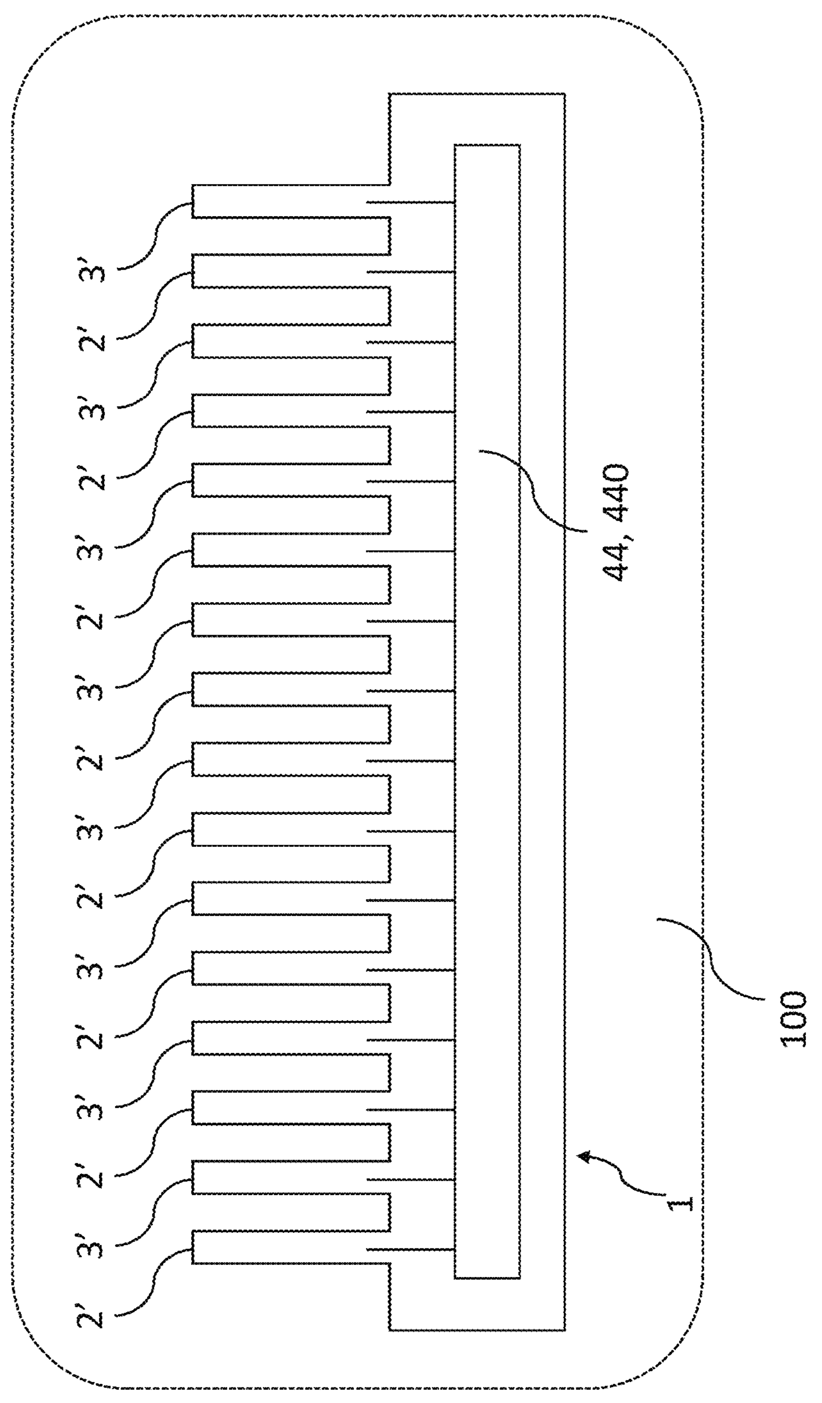
FIG. 6 is a schematic diagram of a chip with multiple cantilever pairs.

FIG. 6 shows a further embodiment of the sensor 1. The sensor 1 here comprises multiple cantilever pairs, where each cantilever pair here comprises a reference cantilever 3' and a test cantilever 2'. The reference cantilever 3' and test cantilever 2', or the corresponding transducers, are, as in FIGS. 5A to C, electrically connected to one another via an electrode circuit, such that a cross-bridge voltage VB' can be tapped off for each cantilever pair. The cross-bridge voltage VB' may be tapped off from each cantilever pair by the A/D converter 440, or by the cross-bridge voltage detector 44. In particular, the measured signal from a specific cantilever pair may, for example, be output in the A/D converter 440 via an A/D converter logic unit, or the integrated measured signal from all cantilever pairs may be output, or a combination thereof. It is thus possible in particular to average the measured signals over various cantilever pairs, such that the occurrence of an analyte 90 is indicated with higher statistical significance. However, it is also possible for various reference and receptor layers 34, 24 to be applied to the different cantilever pairs, such that such a sensor 1 may be used to analyse the sample 9 for different analytes 90 at the same time. For example, however, it is also possible for a single reference cantilever 3 to serve as reference for multiple test cantilevers 2.

In particular, the sensor 1 is formed with the multitude of cantilever pairs on a chip 100. A chip here may mean that the sensor 1 has been fabricated from a single substrate, such that, for example, the various cantilevers 2, 3 are mechanically connected to one another. However, it may also be the case that the chip 100 comprises a further electronic circuit, which is, for example, a CMOS circuit, i.e. a semiconductor circuit that taps off the cross-bridge voltage VB' and directly processes it further. Such a semiconductor circuit in combination with a sensor is also called a system-on-a-chip.

Figure 7:
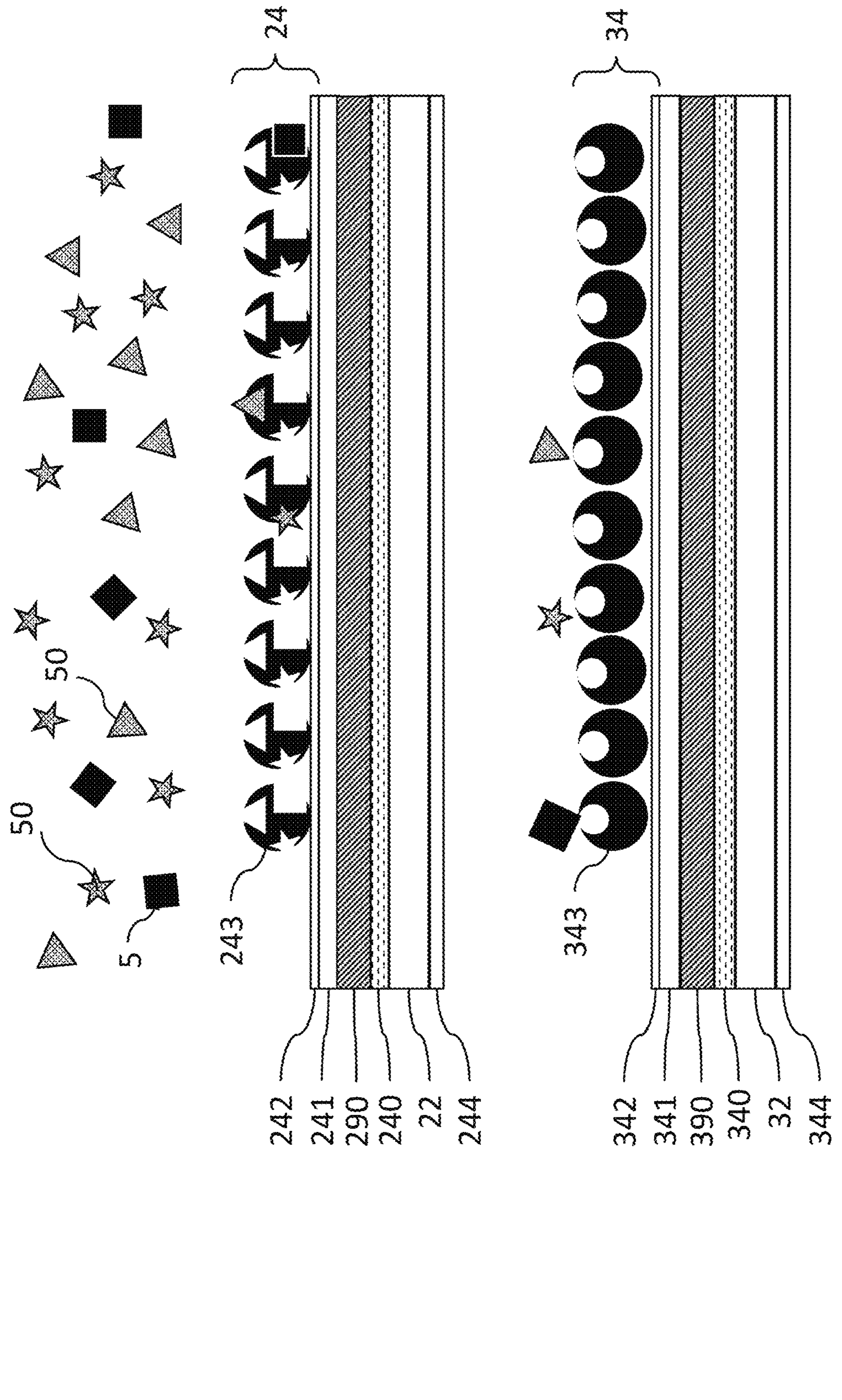
FIG. 7 is a schematic diagram of the binding of antigens to antibodies.

FIG. 7 shows a schematic of the structure of the various deformable parts 22, 32 of the reference and test cantilevers 3, 2. The construction of the cantilevers is identical apart from the receptor layer and the reference layer, meaning that an interaction with the sample or the surrounding medium, along with the mechanical design of the cantilever, is very substantially identical.

A reference converter layer 340 or a test converter layer 240 have respectively been applied atop the deformable part 32, 22 of the reference cantilever or test cantilever 3, 2, and these firstly form electrodes for reference or test transducer (not shown in FIG. 7) and secondly optionally promote adhesion between the surface of the deformable part 32, 22 and a reference function layer 390 or test function layer 290.

A monolayer 341, 241 may respectively have been applied atop the surface of the reference function layer 390 or test function 290, and a receptor layer 242 or a reference layer 342 may have been applied thereon.

The function layer 390, 290 has the function of creating an asymmetric layer structure of the cantilever 3, 2, so as to give a maximum difference in the upper surface area of the cantilever and a lower surface area of the cantilever. The converter layer 340, 240 may especially comprise gold or consist of gold, where the transducers are correspondingly contact-connected via the electrodes arranged in the converter layer 340, 240.

By means of the function layer 390, 290, an electrical insulation may also be applied atop the converter layer 340, 240, especially the converter layer 340, 240 comprising gold or consisting of gold, in order to provide insulation from the environment.

The function layer 390, 290 may also serve to compensate for the surface unevenness or trenches caused by the structuring of the electrodes of the converter layer 340, 240 and/or the formation of the transducers.

It is possible to apply a so-called self-assembly monolayer 341, 241 atop the function layer 390, 290, which is able to compensate for the remaining surface unevenness of the function layer 390, 290 beneath and simultaneously provides for promotion of adhesion for further layers, namely the reference or receptor layers 34, 24.

The structure of the reference layer or receptor layer 34, 24 may be different and may be matched to the respective demands of the analysis.

In a preferred embodiment, however, both layers are based on a layer that may comprise so-called protein A 242, which binds firstly to the self-assembly monolayer 241, 341, but also has and can bind to antibodies 243 or isotype control antibodies 343 on its surface.

The antibodies 243 are proteins that react or bind to an antigen 5 and hence, for example, mark virus cells in the human immune system, such that the immune system is accordingly able to destroy the marked virus in order, for example, to stem or to prevent a viral outbreak. The antibodies 243 are very substantially specific to the antigen 5, but may also interact with other similar antigens 50. FIG. 7 shows that the antibody 243 can interact with the antigen 5 and the similar antigens 50 to some degree.

In contrast to the antibody 243, the isotype control antibody 343 is a protein that preferentially with ultrahigh specificity does not interact with the antigen 5. This makes it possible to virtually rule out any interaction with a specific antigen 5. This is shown in FIG. 7 in that the isotype control antibody 343 can interact only with two similar antigens 50, but not with the one shown schematically as a square here.

Because the test cantilever 2 has an antibody 243 and the reference cantilever 3 has an isotype control antibody 343, it is ensured that, in the sample 9, the analyte 90, if the analyte 90 is an antigen 5, can only interact here with the test cantilever 2. This ensures that the relative deformation brought about by the analyte in the test cantilever 2, in comparison with the deformation of the reference cantilever 3, is based solely on the presence of the analyte 90 or of the antigen 5. Accordingly, it is possible with this sensor 1 to reliably and quickly detect an antigen 5.

In contrast to the upper surface of the cantilevers, the lower surface of the cantilevers is passivated. Such a passivation may have the effect that an interaction, or binding, or absorption or adsorption, of an analyte 90 in the sample 9 in or on the cantilevers is avoided. However, such a passivation layer in particular also contributes to an increase in the asymmetry of the layer structure in order to bring about the greatest possible extension effect on the upper surface of the cantilever 3, 2. In particular, the passivation layer may comprise trimethoxysilane and/or a blocking substance.

The sensor shown can in particular be used to detect the antigens 5 of a Sars-CoV2 virus or of another virus. For this purpose, the receptor layer 24 of the test cantilever 2 comprises Sars-CoV2 antibodies, for example, while the reference layer 34 comprises Sars-CoV2-specific isotype control antibodies. A measured signal is accordingly generated by the sensor 1 when the antigens 5 of a Sars-CoV2 virus are present in the sample 9 and these accumulate on the test cantilever 2 or the receptor layer 24.

Figure 8:
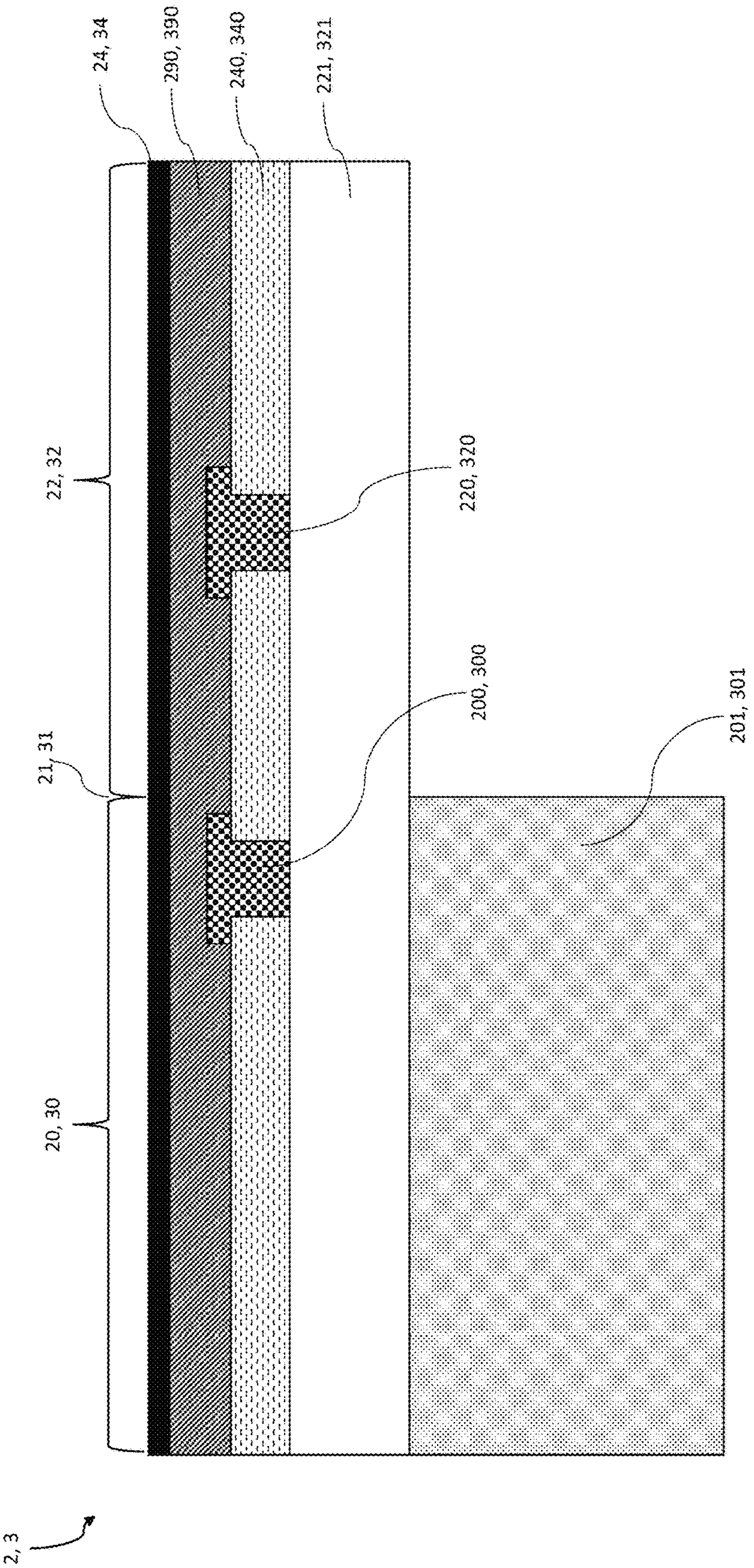
FIG. 8 is schematic diagram of the sensor in the form of a cantilever with a function layer that covers the sensor layer.

FIG. 8 shows a schematic of a reference cantilever 3 or test cantilever 2. The cantilever 3, 2 is divided into base 30, 20 and a deformable part 32, 22, where the boundary between the base 30, 20 and the deformable part 32, 22 is at the bending edge 31, 21.

In the embodiment shown, the reference cantilever 3 or test cantilever 2 comprises or is composed of multiple layers. The cantilever 3, 2 here comprises a main body 301, 201 which comprises or has been manufactured from silicon, for example, atop which has been applied a first carrier layer 321, 221, consisting of SiN for example, that project beyond the edge of the main body 301, 201 and hence extends beyond base 30, 20 and the deformable part 32, 22, and hence in structural terms also forms the deformable part 32, 22 of the cantilever 3, 2.

In addition, the cantilever 3, 2 comprises a test converter layer 240 or reference converter layer 340 which is formed as a conductive layer and is formed to electrically connect a passive reference or test transducer 300, 200 on the base 30, 20 and an active reference or test transducer 320, 220 on the deformable part 32, 22. In the test converter layer 240 or reference converter layer 340, it is possible to provide correspondingly structured conductor tracks that form the intended conductor structure for contact connection of the respective transducers.

The respective transducers 300, 320, 200, 220 may be accommodated in the respective converter layer 340, 240. In other words, the structure of the conductor tracks of the converter layer may be formed in such a way that the transducers 300, 320, 200, 220 are in direct contact with or have been applied atop the first carrier layer 321, 221, and the conductor tracks adjoin them laterally.

The converter layer 340, 240, which is in the form of a conductive layer in the design shown, for the purpose of increased surface extension in the converter layer, may simultaneously serve as activation layer, such that the sensitivity of the active reference or test transducer 320, 220 is increased on deformation of the cantilever.

As indicated in the figure by the gaps in the converter layer 340, 240 at the sites of the active and passive reference or test transducer 300, 200 and 320, 220, the converter layer 340, 240 formed as a conductive layer is structured for suitable electrical contact connection of the reference or test transducer 320, 220, 300, 200 to electrodes.

The cantilever 3, 2 also comprises a test function layer or reference function layer 390, 290 arranged between the converter layer 340, 240 and a receptor layer or reference layer 34, 24. In the embodiment shown, the function layer 390, 290 covers the complete area of the converter layer 340, 240, including the active and passive reference or test transducer 320, 220 and 300, 200. The receptor layer or reference layer 32, 22 has been applied on the outer surface of the function layer 390, 290 in order to ensure direct contact with a sample to be examined.

The test function layer 290 or reference function layer 390 can thus, for example, compensate for or at least reduce the surface unevenness caused by the structuring of the electrodes in the converter layer 340, 240.

The test function layer 290 or reference function layer 390 can thus also achieve, for example, electrical insulation of the electrodes in the converter layer 340, 240 and of the transducers 200, 220, 300, 320 with respect to the receptor layer or reference layer 32, 22.

Figure 9A:
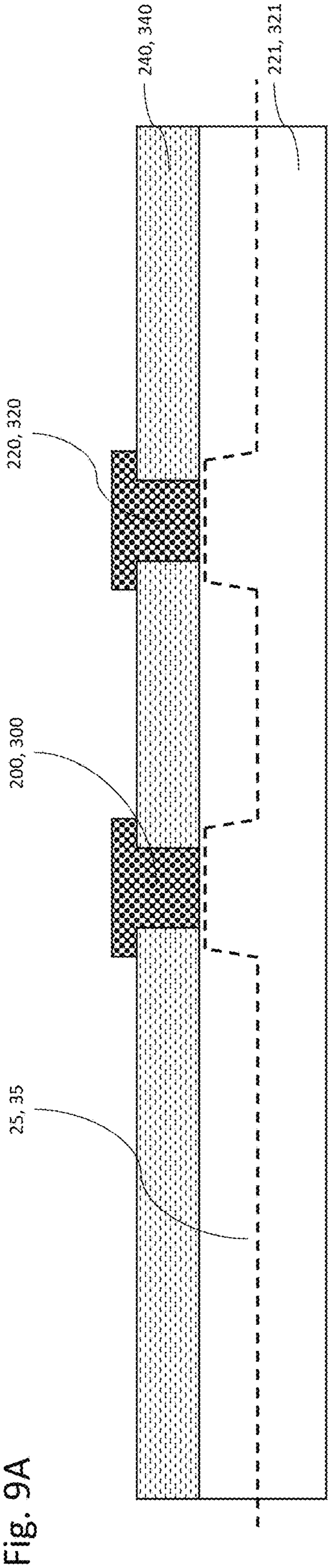

For example, FIG. 9A shows a layer structure of the cantilever, especially comprising a carrier layer 321, 221 and a converter layer 340, 240, and also passive transducers 300, 200 and active transducers 320, 220.

In addition, a neutral axis 35, 25 of the cantilever 3, 2 is drawn in the form of a dotted line.

The neutral axis 35, 25 is characterized in that no change in length takes place along said axis on bending of the cantilever. As shown for example in the figure, the line of the neutral axis is influenced significantly by the layer structure. In the case of inhomogeneous material, especially a material with a homogeneous module of elasticity, the neutral axis runs along the geometric middle of the material (considering bending/deformation of the material transverse to this neutral axis).

In the case of multiple layers and possibly different moduli of elasticity and thicknesses of the layers involved, the neutral axis may also lie away from the geometric middle of the layer structure, as illustrated by the corresponding equation in the general part of the description.

The neutral axis 35, 25 should preferably be as far as possible away from the active transducers in order to maximize the sensitivity of the sensor. In other words, the neutral axis 35, 25 preferably lies such that the change in surface tension or change in length at the position of the active transducers is at a maximum.

However, the neutral axis 35, 25 in FIG. 9A shows a deviation at those positions where the transducers 300, 200 and 320, 220 are positioned. Typically, the effect of the material of the transducers is a shift in the neutral axis directed toward the transducers. This creates a comparatively reduced change in length compared to the rest of the layer structure at the positions of the transducers on bending or variation of the surface tension, which reduces the sensitivity of the sensor.

Figure 9B:
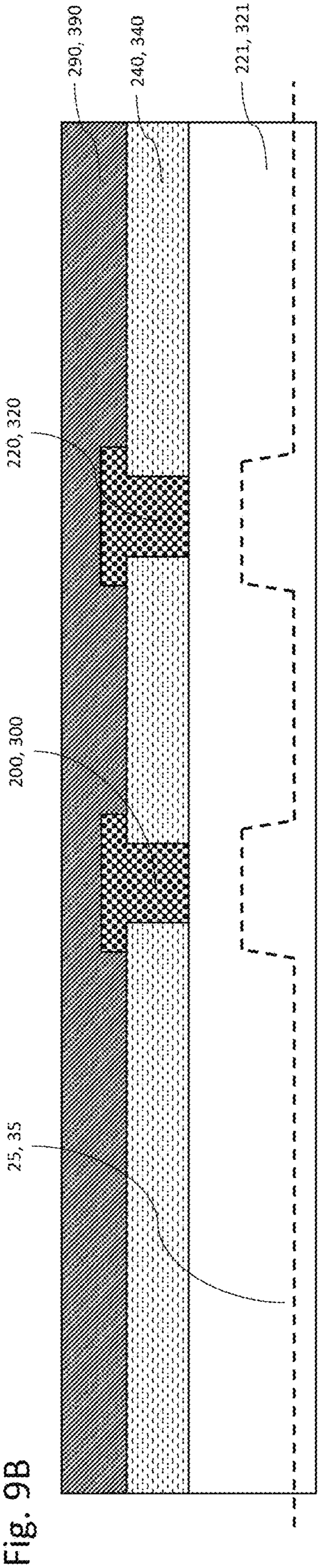
FIG. 9B is a schematic diagram of selected layers of a cantilever with additional function layer and a neutral axis shifted downward.

In order to counter this unwanted effect, in FIG. 9B, according to a preferred embodiment, a function layer 390, 290 has been applied atop the converter layer 340, 240. The applying of the function layer 390, 290 can move the neutral axis 35, 25 within the layer structure.

This is shown in FIG. 9B. By comparison with the neutral axis 35, 25 from FIG. 9A, the neutral axis in FIG. 9B has been shifted downward. In order to move the neutral axis 36, 25 downward by means of this additional function layer 340, 240, in this embodiment, the modulus of elasticity of the function layer 340, 240 must be much smaller than the modulus of elasticity of the layer structure beneath. In addition, the thickness of the function layer 340, 240 must be sufficiently small in order to induce the shift shown of the neutral axis 35, 25 away from the transducers.

Figure 10:
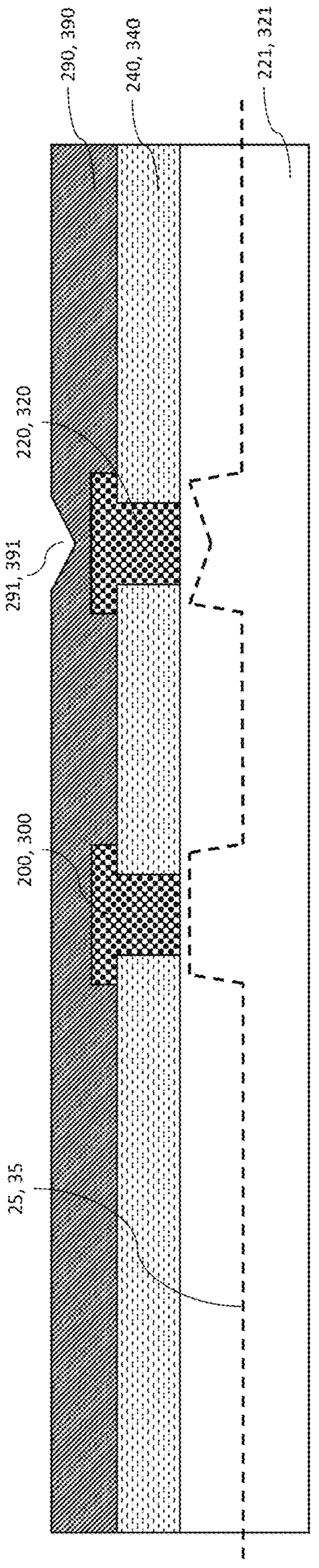
FIG. 10 is a schematic diagram of selected layers of a cantilever with additional function layer and a neutral axis shifted downward at the structuring site.

FIG. 10 shows essentially the same arrangement as FIG. 9B, except that structuring of the height profile of the function layer 390, 290 is shown in schematic form here, which is represented for example as a recess 391, 291 at the site of the active reference or test transducer 320, 220. As shown in FIG. 10, the change in the height profile of the function layer 390, 290 can influence the line of the neutral axis 35, 25 in such a way that the neutral axis is at a distance from the transducer at the site thereof.

The recess 391, 291 achieves a controlled influence on the stress distribution of the cantilever 3, 2, which is preferably such that the extension under deformation of the deformable part 32, 22 of the cantilever 3, 2 is at a maximum at the site of the active reference or test transducer 320, 220.

It should be pointed out that it is possible also to apply a receptor layer 34, 24 atop the structured function layer 390, 290.

Figure 11A:
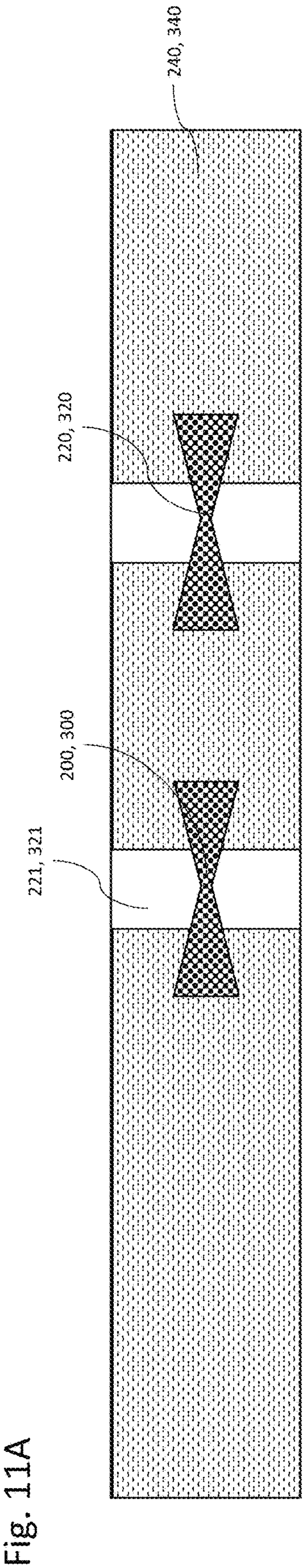
FIG. 11A is a top view of the converter layer of a cantilever with transducers structured in the plane.

FIG. 11A shows a top view of a cantilever, in particular of the carrier layer 321, 221, and of the converter layer 340, 240 on top, into which the passive transducers 300, 200 and the active transducers 320, 220 have been embedded.

For example, the converter layer 340, 240 may consist of gold or comprise gold, and comprise electrodes, i.e. an electrical connection for the transducers. As shown in FIG. 11, the transducers are structured in a non-trivial form. A trivial form here would correspond typically to a rectangular shape. The structuring can achieve a non-homogeneous distribution of stress in the transducers.

Figure 11B:
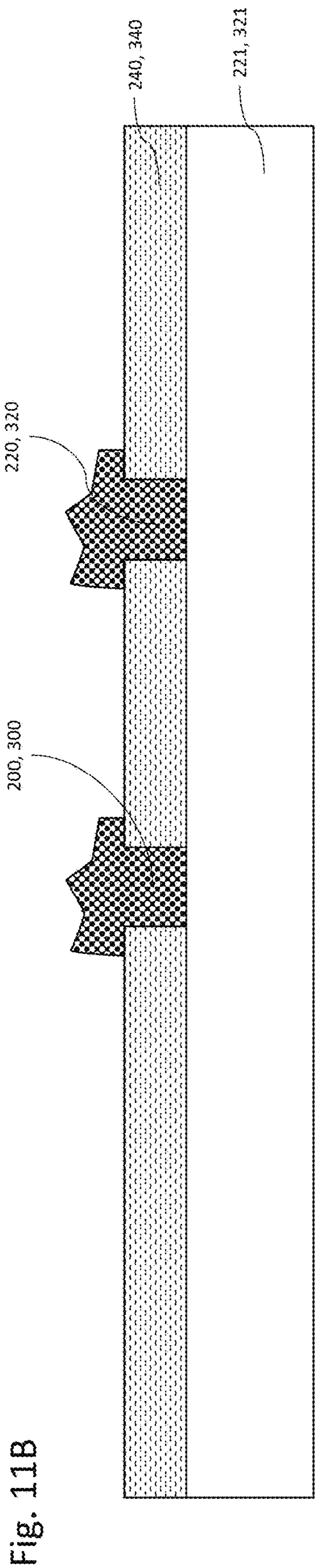
FIG. 11B is a lateral view of selected layers of a cantilever with structured height profile of the transducers

FIG. 11B shows a cantilever layer structure comprising a carrier layer 321, 221 and a converter layer 340, 240, where the passive transducers 300, 200 and the active transducers 320, 220 have a non-trivial form with regard to their height profile. A trivial form here would correspond to a flat height profile of the transducers. Such structuring of the height profile of the transducers can bring about a controlled influence on the stress distribution and an influence on the neutral axis at the site of the transducers themselves. It is possible here to configure the structuring in such a way that the stress distribution at the respective site of the transducers is optimized, i.e. the change in length in particular is maximized on bending of the cantilevers at the site of the transducers.

Where applicable, all individual features that are illustrated in the embodiments may be combined with one another and/or exchanged for one another without departing from the scope of the invention.

LIST OF REFERENCE SIGNS

1 sensor
10 bending edge
2 test cantilever
20 base
201 main body
21 bending edge
200 passive test transducer
22 deformable part
221 carrier layer
220 active test transducer
24 receptor layer
25 neutral axis of the test cantilever
240 test converter layer
241 self-assembly monolayer
242 protein A
243 antibody
244 passivation layer
26 surface
260 upper surface
262 lower surface
290 test function layer
291 recess
3 reference cantilever
30 base
301 main body
31 bending edge
300 passive reference transducer
32 deformable part
321 carrier layer
320 active reference transducer
34 reference layer
35 neutral axis of the reference cantilever
340 reference converter layer
341 self-assembly monolayer
342 protein A
343 isotype control antibody
344 passivation layer
36 surface
360 upper surface
362 lower surface
390 reference function layer
391 recess
4 electronics
40 electrode
400, 401, 402, 403 electrodes
42 cross-bridge voltage detector
44 A/D converter
440 A/D converter logic unit
5 antigen
50 other antigen
F force
L deflection
D extension
AT distance between active and passive transducer
AE distance between electrodes
S axis of symmetry
VB cross-bridge voltage

The invention claimed is:

1. A sensor for conversion of at least one of chemical and biochemical information from at least one analyte in a sample to an electrical signal, the sensor comprising:

a test cantilever having a base and a deformable part, with a receptor layer configured for selective uptake of the at least one analyte applied at least atop the deformable part, the test cantilever having a test converter layer that includes a passive test transducer on the base and an active test transducer on the deformable part, and wherein a test function layer is disposed between the test converter layer and the receptor layer; and a reference cantilever having a base and a deformable part, with a reference layer configured for selective non-uptake of the at least one analyte applied atop the deformable part, the reference cantilever having a reference converter layer that includes a passive reference transducer on the base and an active reference transducer on the deformable part, and wherein a reference function layer is disposed between the reference converter layer and the reference layer, wherein at least one of the test function layer and the reference function layer are geometrically structured so as to maximize a deformation in at least one of the active test transducer and the active reference transducer, respectively, that is induced by deformation of the respective deformable part, and wherein the test and reference function layers comprise a modulus of elasticity that is smaller than the average modulus of elasticity of the test and reference converter layers, and wherein the test and reference function layers further comprise a recess that forms a reduced thickness of the test and reference function layers in a thickness direction thereof and at a site for the at least one of the active test transducer and the active reference transducer.

2. The sensor according to claim 1, wherein the active and passive reference transducers and the active and passive test transducers are configured to output the electrical signal corresponding to at least one of the occurrence, the concentration and the amount of the at least one analyte in the sample.

3. The sensor according to claim 1, wherein the test function layer covers at least one of the active test transducer and the passive test transducer, and the reference function layer covers at least one of the active reference transducer and the passive reference transducer.

4. The sensor according to claim 1, wherein the test function layer forms a flat surface that accommodates the receptor layer.

5. The sensor according to claim 1, wherein the reference function layer forms a flat surface that accommodates the reference layer.

6. The sensor according to claim 1, wherein the test function layer and the reference function layer comprise a same material.

7. The sensor according to claim 1, wherein a material of at least one of the test function layer and the reference function layer is configured to adjust a surface energy in order to facilitate at least one of a binding of the receptor layer to the test function layer and a binding of the reference layer to the reference function layer.

8. The sensor according to claim 1, wherein at least one of the test function layer and the reference function layer comprises an electrically insulating material.

9. The sensor according to claim 1, wherein at least one of the test function layer and the reference function layer comprises a porous material that enables partial permeability to at least one of selected substances and analytes.

10. The sensor according to claim 1, wherein the test converter layer comprises electrodes configured to contact at least one of the passive test transducer and the active test transducer, and the electrodes are covered by the test function layer.

11. The sensor according to claim 1, wherein the reference converter layer comprises electrodes configured to contact at least one of the passive reference transducer and the active reference transducer, and the electrodes are covered by the reference function layer.

12. The sensor according to claim 1, further comprising a passivation layer arranged atop a lower surface of at least one of the test cantilever and a lower surface of the reference cantilever.

13. The sensor according to claim 12, wherein the passivation layer is configured to minimize adhesion of the at least one analyte on the lower surface of the at least one of the test cantilever and the reference cantilever.

14. The sensor according to claim 1, further comprising at least one of a receptor layer for selective uptake of the at least one analyte and a reference layer for non-selective uptake of the at least one analyte, wherein the receptor layer and the reference layer are arranged on the lower surface of the at least one of the test cantilever and the reference cantilever, respectively.

15. The sensor according to claim 14, wherein a change in a surface tension of an upper surface as a result of binding of the at least one analyte to the receptor layer and/or the reference layer is opposite of a change in a surface tension of the lower surface of the respective cantilever.

16. The sensor according to claim 1, wherein material properties of at least one of the test function layer and the reference function layer are configured to maximize a deformation in the active test transducer or the active reference transducer, respectively, induced by deformation of the deformable part of the test cantilever or the reference cantilever.

17. The sensor according to claim 16, wherein the material properties are one of a thickness and a modulus of elasticity of the respective function layer.

18. The sensor according to claim 1, wherein at least one of the active test transducer and the active reference transducer is structured in a horizontal plane of the respective cantilever, such that a sensitivity of the respective transducer is optimized by a maximization of a deformation or change in length at a site of the respective transducer.

19. The sensor according to claim 1, wherein at least one of the active test transducer and the active reference transducer is geometrically structured such that a sensitivity of the respective transducer is optimized by a maximization of a deformation or a change in length at a site of the respective transducer, and wherein at least one of a spatially long side of the active test transducer and a spatially long side of the active reference transducer is aligned parallel to a main component of a deformation of the respective deformable part of the respective cantilever.

* * * * *